US008431618B2

(12) United States Patent
Endo et al.

(10) Patent No.: US 8,431,618 B2
(45) Date of Patent: Apr. 30, 2013

(54) PROCESSED STARCH POWDER WITH EXCELLENT DISINTEGRATION PROPERTIES AND MANUFACTURING METHOD THEREOF

(75) Inventors: Masaaki Endo, Tokyo (JP); Shozo Kaneyama, Tokyo (JP); Kazuhiro Obae, Tokyo (JP); Ichiro Ibuki, Tokyo (JP); Michihiro Sunako, Kashihara (JP); Eishi Wakamiya, Kashihara (JP)

(73) Assignees: Asahi Kasei Chemicals Corporation, Tokyo (JP); Sanwa Cornstarch Co., Ltd., Nara (JP)

( * ) Notice: Subject to any disclaimer, the term of this patent is extended or adjusted under 35 U.S.C. 154(b) by 0 days.

(21) Appl. No.: 12/935,394

(22) PCT Filed: Mar. 30, 2009

(86) PCT No.: PCT/JP2009/056482
§ 371 (c)(1),
(2), (4) Date: Sep. 29, 2010

(87) PCT Pub. No.: WO2009/123102
PCT Pub. Date: Oct. 8, 2009

(65) Prior Publication Data
US 2011/0021643 A1 Jan. 27, 2011

(30) Foreign Application Priority Data
Mar. 31, 2008 (JP) ................................ 2008-090807

(51) Int. Cl.
*A61K 47/26* (2006.01)
*A23L 1/0522* (2006.01)
*C13K 1/06* (2006.01)
*C08B 30/12* (2006.01)

(52) U.S. Cl.
USPC ............... 514/778; 127/32; 127/38; 426/661

(58) Field of Classification Search ........................ None
See application file for complete search history.

(56) References Cited

U.S. PATENT DOCUMENTS

| 455,177 | A | 6/1891 | Delaney |
|---|---|---|---|
| 3,622,677 | A | 11/1971 | Short et al. |
| 4,072,535 | A | 2/1978 | Short et al. |
| 4,369,308 | A | 1/1983 | Trubiano |
| 4,447,601 | A | 5/1984 | Takeo et al. |
| 5,164,014 | A | 11/1992 | Brancq et al. |
| 5,362,329 | A | 11/1994 | Yoshino et al. |
| 5,616,343 | A | 4/1997 | Cartilier et al. |
| 6,143,324 | A | 11/2000 | Michaud et al. |
| 6,455,069 | B1 | 9/2002 | Michaud et al. |
| 7,612,198 | B2 | 11/2009 | Fuertes et al. |
| 2004/0151767 | A1 | 8/2004 | Okoniewska et al. |
| 2006/0008521 | A1 | 1/2006 | Zhang et al. |
| 2006/0204569 | A1* | 9/2006 | Obae et al. ............ 424/464 |

FOREIGN PATENT DOCUMENTS

| JP | 48-68726 | 9/1973 |
|---|---|---|
| JP | 53-5725 | 10/1974 |
| JP | 52-066619 | 6/1977 |
| JP | 58-27774 | 7/1978 |
| JP | 62-7201 | 8/1978 |
| JP | 56-11689 | 2/1980 |
| JP | 58-32828 | 2/1983 |
| JP | 59-47600 | 11/1984 |
| JP | 63-7531 | 1/1988 |
| JP | 4-130102 | 5/1992 |
| JP | 4-318001 | 11/1992 |
| JP | 6073101 A | 3/1994 |
| JP | 8-507769 | 8/1996 |
| JP | 11-269202 | 10/1999 |
| JP | 3004758 | 1/2000 |
| JP | 2001-39894 | 2/2001 |
| JP | 2004-137230 | 5/2004 |
| JP | 2004-238622 | 8/2004 |
| JP | 2005-213496 | 8/2005 |
| JP | 2006-001924 | 1/2006 |
| JP | 2006-45222 | 2/2006 |
| JP | 2006-176496 | 7/2006 |
| JP | 2007-001875 | 1/2007 |
| JP | 2007-001999 | 1/2007 |
| WO | 96/22110 | 7/1996 |
| WO | 2005/005484 | 1/2005 |

OTHER PUBLICATIONS

English language translation of claims and bibliography data of JP 62-7201, Aug. 30, 1978.
English language translation of claims and bibliography data of JP 53-5725, Oct. 22, 1974.
English language translation of claims and bibliography data of JP 48-68726, Sep. 19, 1973.
International Search Report for PCT/JP2009/056482, mailed Jun. 30, 2009.

* cited by examiner

*Primary Examiner* — Suzanne Ziska
(74) *Attorney, Agent, or Firm* — Greenblum & Bernstein, P.L.C.

(57) ABSTRACT

Disclosed are a processed starch powder in which the amount of water soluble component is greater than 2 wt % but less than 10 wt %, the water retention amount is greater than 600% and 1500% or less, and which comprises nonbirefringent particles, and a manufacturing method thereof.

16 Claims, 17 Drawing Sheets

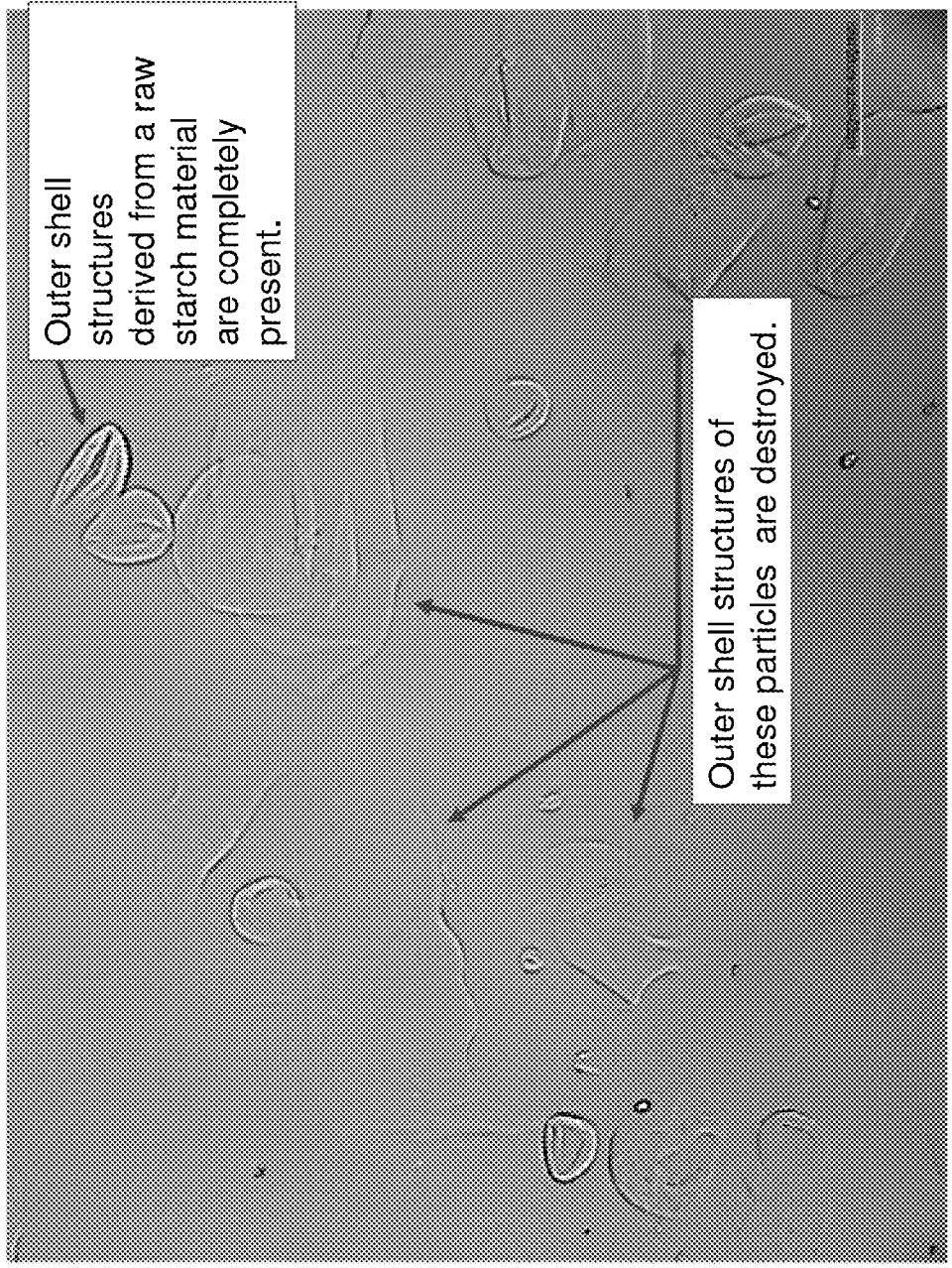

PROCESSED STARCH POWDER WITH EXCELLENT DISINTEGRATION PROPERTIES AND MANUFACTURING METHOD THEREOF

TECHNICAL FIELD

The present invention relates to a processed starch powder acting as a disintegrant in a solid preparation, a composition comprising the processed starch powder and one or more active ingredients and a method for manufacturing the processed starch powder. More specifically, the present invention relates to a processed starch powder capable of enhancing the disintegration rate of a solid preparation containing an active ingredient or enhancing the release of an active ingredient from a solid preparation in the use of pharmaceuticals, agricultural chemicals, fertilizers, feed, food, industries, cosmetics, etc.

BACKGROUND ART

The preparations containing an active ingredient used in the fields of pharmaceuticals, agricultural chemical, fertilizers feed, food, industries, cosmetics, etc., are desired, in many cases, to be quickly disintegrated for the immediate expression of active ingredient effects when placed in an intended environment. Conventionally, disintegrants are generally used to improve the disintegrating properties of these solid preparations. Examples of the disintegrant include cellulose derivatives such as carmellose calcium (calcium carboxymethyl cellulose), croscarmellose sodium (crosslinked sodium carboxymethyl cellulose), cellulose derivatives such as low substituted hydroxypropyl cellulose, chemical synthetics such as crospovidone (crosslinked polyvinyl pyrrolidone), starch derivatives such as carboxymethyl starch sodium and hydroxypropyl starch, plant rubbers such as guar gum and sodium alginate, and starches such as partly pregelatinized starch.

However, metal salts such as carmellose calcium, croscarmellose sodium, hydroxypropyl starch were not always satisfactory because, when mixed with an active ingredient, or the like, showing the reactivity to a metal salt, the active ingredient is decomposed during storage resulting in a reduced content, coloring, or the like. Further, hydroxypropyl starch, low substituted hydroxypropyl cellulose, and like celluloses or starch polymers in which a hydrophobic substituent is introduced are nonionic but the hydrophobic substituent itself was sometimes reactive to a drug. For this reason, the problems such as the decomposition of an active ingredient or the development of coloring during storage were posed and thus they were not always satisfactory. Furthermore, crospovidone (crosslinked polyvinyl pyrrolidone) is considered to have a comparatively low interaction with a drug but is characterized as being highly hygroscopic. Thus, crospovidone had drawbacks in that the decomposition of an active ingredient was caused which was promoted by the presence of moisture such as the ester bond, a solid preparation was swollen due to the moisture absorption and stuck to other solid preparations or a container, the hardness and friability of a solid preparation were reduced, or the like. The tablet in a PTP package, when absorbing moisture over time causing the reduction of hardness, becomes useless for practical application due to the occurrence of the breakage or cracks. Further, since crospovidone is a chemically polymerized product, a monomer (vinyl pyrrolidone) toxic to human body and a chemical contaminant (hydrazine) are mixed in, which hence has been problematic. Sodium alginate, agar, and the like, have not been in much use as a disintegrant because they have drawbacks as being expensive, having poor compression properties, and the like.

Starches, represented by raw starch (β-starch) and partly pregelatinized starches in which a part of raw starches are gelatinized, have been used as disintegrants which are less reactive to a drug and have low hygroscopicity. The processed starches, in which raw starch is physically modified, have been widely used as disintegrants because the starch swelling properties can be enhanced by a method such as changing the level of gelatinization, or the like, they have a low reactivity to an active ingredient due to chemically being the same as raw starch, they are inexpensive, and they have been commonly eaten and very safe. However, these starches (PATENT DOCUMENTS 1 to 9 and 11 to 19), compared with synthetic products such as croscarmellose sodium, crospovidone, etc., have poorer disintegrating properties and thus require to be added in a large amount for imparting satisfactory disintegrating properties, consequently limiting the amount of an active ingredient to be added.

PATENT DOCUMENT 1 describes that a processed starch having a swelling degree (which corresponds to the water retention capacity of the present invention) of 3.0 to 6.0 can be used as a disintegrant, however; the swelling degree is 3.0 to 6.0 and is different from the range of the present invention. According to PATENT DOCUMENT 1, the processed starch is obtained by a method in which a starch is completely gelatinized by being extruded at a low pressure using an extruder having a small screw compression ratio, or like method, subsequently cooled to crystallize a part of the gelatinized starches, followed by being dried and crushed to adjust the particle size. Accordingly, since such a processed starch has at least a part of the starch particles broken due to the mechanical force applied during the gelatinization process and hence the outer shell structure damaged, the stress applied to the surroundings by the swell is diminished, thereby providing insufficient disintegrating force. The disintegration time of the tablet used in Examples of this PATENT DOCUMENT is 3.9 to 8.3 minutes when the processed starch is added in an amount of 10% by weight, whereas the disintegration time is 20 seconds or less when the processed starch powder of the present invention is used in the same formula. Thus, the processed starch described in PATENT DOCUMENT 1 is clearly different in the disintegrating force from the processed starch of the present invention. The processed starch of the present invention is effective even when added in an amount of 5% by weight or less. The method described in PATENT DOCUMENT 1 also differs from the present invention in the aspect of comprising a cooling step after heating.

PATENT DOCUMENT 2 describes an aggregate of a natural starch and a pregelatinized starch which contains 1 to 20% by weight of the pregelatinized starch and 80 to 99% by weight of the natural starch, and has a size of 100 to 500 μm. Since the processed starch of the present invention has an average particle size of the primary particles of 25 to 80 μm and most of the particles do not form aggregates, it is different from PATENT DOCUMENT 2 in the aspect of the size of dry particles. Further, the aggregate of this invention of PATENT DOCUMENT 2 is formed by granulating the pregelatinized starch and the natural starch, and is hence also clearly different from the present invention in that the birefringent property intrinsic to the natural starch is observed. PATENT DOCUMENT 3 describes a starch granule in which β-starch is mutually bonded with 1 to 4% by weight of pregelatinized starch grains, but the starch granule is different from the processed starch of the present invention in that the birefringent property intrinsic to the β-starch is observed. Further, the invention of the above document is also different from the present invention in the aspect of mixing the β-starch and a pregelatinized starch aqueous solution (a state of mist droplet) and in the aspect of not including a heating process. Furthermore, the amounts of the starch granule added in Examples of said PATENT DOCUMENT are required as much as 17% by weight and 87% by weight, whereas the processed starch of the present invention can impart sufficient disintegrating properties even when added in an amount of 5% by weight or less. PATENT DOCUMENT 4 discloses a method for producing a granule and a tablet by the granulation and compression using as a binder and a disintegrant β-starch with the surface being gelatinized, and PATENT DOCUMENT 5 discloses a method for producing β-starch with the surface being gelatinized. However, the starch of PATENT DOCUMENT 4 comprises 60% by weight of the β-starch and the starch of PATENT DOCUMENT 5 comprises 80 to 95% by weight of the β-starch, exhibiting the birefringent property intrinsic to the β-starch. In these aspects, these starches are different from the processed starch of the present invention. The β-Starch is treated using steam at 100 to 120° C. and immediately fluidized bed dried in PATENT DOCUMENTS 4 and 5, whereas the present invention includes a step of heat treatment using steam at 100 to 130° C. under a reduced pressure condition to prepare a starch slurry and a step of further heating the starch slurry, followed by drying (spray drying). Thus, the present invention is also different in this regard from PATENT DOCUMENTS 4 and 5. The amount of the starch granule added in Examples of these PATENT DOCUMENTS is required as much as 30% by weight, whereas the processed starch of the present invention can impart sufficient disintegrating properties even when added 5% by weight or less. Since natural or β-starch powder has particles having a swelling ratio of as small as about 1.2 times or less and the disintegrating force is hence low, the processed starches of PATENT DOCUMENTS 2 to 5 consisted largely of these particles fail to attain a sufficient disintegrating force and are clearly different from the processed starch of the present invention having a particle swelling ratio of 1.5 time or more with a good disintegrating force.

PATENT DOCUMENT 6 discloses a processed starch powder which practically preserves the outer shell structure, contains 10% by weight or less of a cold water soluble component (which corresponds to the water soluble component of the present invention), has a swelling volume (which corresponds to the sedimentation volume of the present invention) of 3 to 15 ml/g and a water retention potential of about 2 or higher. Further, PATENT DOCUMENT 7 discloses a starch powder containing less than 10% by weight of a cold water soluble component (which corresponds to the water soluble component of the present invention), having a swelling volume (which corresponds to the sedimentation volume of the present invention) of 5 to 15 ml/g and having more nonbirefringent particles than birefringent particles. The processed starches of PATENT DOCUMENTS 6 and 7 are those heat-treated in the presence of water at a temperature of about 10° C. higher than the gelatinization temperature intrinsic to the starch or lower, and imparted with enhanced swelling properties without breaking the starch particles. However, in PATENT DOCUMENTS 6 and 7, since the heating temperature is as low as a temperature of about 10° C. higher than the gelatinization temperature or lower, the effect to enhance the swelling properties of the starch particles was little. The swelling ratio of the processed starch powder made from cornstarch obtained by the methods described in PATENT DOCUMENTS 6 and 7 was as small as about 1.3 and the disintegration time of the tablet was significantly long compared with that of the processed starch of the present invention (see Comparative Example 8 in the present application). In Example 17 of PATENT DOCUMENT 6 in which potato starch was used as a raw material as in the present invention, it is described that the particles were damaged and the water retention capacity exceeded 1500%. Thus, the invention of PATENT DOCUMENT 6 is different from the present invention in the condition of the outer shell structure and the water retention capacity. Further, when Example 15 of PATENT DOCUMENT 7 in which potato starch was similarly used as a raw material was reexamined, the average particle size of the primary particles in the swollen state in water was as small as 35 μm since the heating temperature is as low as a temperature of about 10° C. higher than the gelatinization temperature or lower, resulting in poorer disintegrating properties than the processed starch of the present invention (see Comparative Example 1 of the present invention). The processed starch powders of PATENT DOCUMENTS 6 and 7 are obtained by heating raw starch in the presence of water at a temperature ranging from 50° C. to a temperature of about 10° C. higher than the gelatinization onset temperature or lower, that is one-stage heat treatment, whereas the processed starch of the present invention is obtained by heat-treating a natural starch material (which corresponds to the raw starches in PATENT DOCUMENTS 6 and 7) using steam at a temperature ranging from 100° C. or higher to 130° C. or lower under reduced pressure conditions, subsequently preparing a starch slurry having a solid content of 1 to 20% by weight (which corresponds to the in the presence of water in PATENT DOCUMENTS 6 and 7) and heat-treating at a temperature range from more than a temperature of 10° C. higher than the gelatinization onset temperature intrinsic to starch to less than 90° C., that is two-stage heating of raw starch. Therefore, the processed starch of the present invention is clearly different from those of PATENT DOCUMENTS 6 and 7. Also, the present invention is definitely different in that the temperature range for the heat treatment of the starch slurry, i.e., in the presence of water, is higher than that of PATENT DOCUMENTS 6 and 7.

PATENT DOCUMENT 8 describes an excipient which consists of crystalline cellulose and a modified starch. The modified starch has completely different particle structure from the processed starch of the present invention in the aspects that it does not have the outer shell structure of raw starch due to a partial breakage of the particles caused by the downsizing and that the distinct polarized cross as in cornstarch is found (see FIG. 2 of the PATENT DOCUMENT). Further, since this modified starch contained 10 to 20% by weight of a cold water soluble component (which corresponds to the water soluble component of the present invention) which is more than that of the processed starch of the present invention, the cold water soluble component was dissolved and an adhesive film was formed on the surface or in the pore of a tablet, whereby the permeation of water into a solid preparation was inhibited and a sufficient disintegrating force was not attained. Further, the production method is also different from that of the present invention in the respect of applying a pressure in the presence of water and not including the heating.

PATENT DOCUMENT 9 discloses a processed starch which is mechanically modified, partially pregelatinized, has a sedimentation volume of 1.5 to 9 ml/g and a cold water solubility (which corresponds to the water soluble component of the present invention) of 1 to 8% by weight. The processed starch has most of the particles formed by the continuous engagement of the birefringent part and the mechanically modified nonbirefringent part and hence practically being birefringent particles showing the polarized cross (see FIG. 1 of the PATENT DOCUMENT) which is different from the present invention in the particle structure. The nonbirefringent part in which the outer shell structure of the mechanically modified particle is disrupted has a diminished stress to the surroundings of the starch particle when it absorbs water and swells, and the birefringent part which is not mechanically modified has the swelling properties only equivalent to that of raw starch. For this reason, the processed starch of PATENT DOCUMENT 9 which is the mixture of these particles consequently had a diminished disintegrating force. Further, the starch particle of this invention has an individual starch particle size of as small as 20 μm in water, and hence it is different from the processed starch of the present invention which has the particle size of 50 to 120 μm. Furthermore, as evident from FIG. 3 of PATENT DOCUMENT 9, the swelling ratio of the particles (due to the engagement of several particles there are undistinguishable primary particles derived from the natural starch but the swelling ratio was calculated by selecting only the distinguishable primary particles) is as small as 1.1, and hence the processed starch of PATENT DOCUMENT 9 is different from the processed starch of the present invention having a particle swelling ratio of 1.5 or more. The swelling ratio was the same as that of commercial Starch 1500 (see Comparative Example 7 of the present application). The starch described in this PATENT DOCUMENT is obtained by the extrusion at a formation temperature of 50 to 110° C. and this starch is obviously different in the production method from the present invention. Still furthermore, the amount of the starch granule added in Examples of the PATENT DOCUMENT is required as much as 74.8% by weight, whereas the processed starch of the present invention can impart sufficient disintegrating properties even when added in an amount of 5% by weight or less.

PATENT DOCUMENT 11 discloses a starch powder which is treated by direct compression, partially swollen and has a ratio of non-swelling birefringent particle to swelling nonbirefringent particle of 1:5 to 5:1. Further, PATENT DOCUMENT 12 discloses a preparation comprising partially swollen starch powder containing nonbirefringent starch granule and non-swelling birefringent starch granule in a ratio of 1:5 to 5:1. The processed starches of PATENT DOCUMENTS 11 and 12 are different from the processed starch of the present invention in the aspect that they contain non-swelling birefringent particles in a proportion of one sixth or more, i.e., exceeding 10%, whereas the processed starch of the present invention contains 90% or more of the particles being swelling nonbirefringent particles in which the polarized cross is disappeared. The processed starches of PATENT DOCUMENTS 11 and 12 are the same as that of the present invention in the aspect that they are obtained by heat-treating a starch slurry to cause a partial swelling of the starch grain without disintegrating the starch grain. However, since the heating is carried out at a temperature practically not higher than the gelatinization temperature of the starch, it is difficult to reduce the crystallinity of the starch particle and enhance the swelling properties and, as a result, the non-swelling birefringent particles are contained in a proportion of one sixth or more, i.e., exceeding 10%. Since the non-swelling birefringent starch has almost or totally no disintegrating force, the processed starches of PATENT DOCUMENTS 11 and 12 which contain a large amount of the non-swelling birefringent particles exhibited little disintegrating force. Further, the amount of the starch granule added in Examples of these PATENT DOCUMENTS is required as much as 19 to 59% by weight, whereas the processed starch of the present invention can impart sufficient disintegrating properties even when added in an amount of 5% by weight or less.

PATENT DOCUMENTS 13 and 14 disclose a downsized starch having the particle being crushed due to the downsizing, containing about 4 to 40% by weight of a cold water soluble component (which corresponds to the water soluble component of the present invention) and having a swelling force (which corresponds to the sedimentation volume of the present invention) of 2.5 to 12. Such a processed starch has its particle partially crushed by the downsizing and is different from the processed starch of the present invention in which only the outer shell structure derived from raw starch is preserved, the particle is not crushed and the shape of the starch particle is maintained. The processed starch in which the particles are partially crushed irreversibly swells (dissolves) in water. As a result, the viscosity of a liquid is increased and an adhesive film is formed on the surface or in the pore of a tablet, thereby inhibiting the permeation of water into a solid preparation and failing to achieve a sufficient disintegrating force. Further, the dissolved product posed problems such as the intense reactivity to an active ingredient which developed the coloring of the composition over time, or the like. Furthermore, as shown in FIGS. 2 and 4 of this PATENT DOCUMENT, the birefringent part of the downsized starch exhibits a distinct polarized cross as seen in raw cornstarch. The starch particle having such high crystallinity that the polarized cross is clearly seen had poor swelling properties and failed to achieve a sufficient disintegrating force. The tablet shown in Examples of PATENT DOCUMENTS 13 and 14 contains such a downsized starch in a large amount of 50% by weight or more and is different in the aspect of the disintegrating force from the processed starch of the present invention which is capable of expressing a sufficient disintegrating force when added in an amount of 1 to 5% by weight.

PATENT DOCUMENT 15 discloses a method for producing a tablet containing powder or granular waxy cornstarch. However, the waxy cornstarch of this invention is a natural raw starch itself and has the birefringent properties, and hence it is different from the processed starch of the present invention. The starch composed of solely birefringent particles has an insufficient disintegrating force. As shown in Examples of this PATENT DOCUMENT, such a processed starch requires waxy cornstarch as much as 50% by weight of the tablet and is different in this respect from the processed starch of the present invention which exhibits a sufficient disintegrating force when added in an amount of 1 to 5% by weight.

Further, waxy cornstarch is known to contain 100% by weight of amylopectin which is also different from the processed starch of the present invention wherein the amylopectin content never be 100% by weight because a natural starch containing 20% by weight or more and less than 30% by weight of amylose is used in the present invention.

PATENT DOCUMENT 16 discloses a processed starch which has a water retention capacity of 400% or higher, a disintegration time of 5 hours or more and, when dispersed in water, has 10 to 90% by weight of amylose and amylopectin (which corresponds to the amount of the water soluble component of the present invention) present in the swollen or dissolved state. This processed starch has 10 to 90% by weight of amylose and amylopectin present in the swollen or dissolved state, i.e., the amount of water soluble components, and is different from the present invention in the aspect of the amount range of the water soluble components. This PATENT DOCUMENT further describes steps of further heating at 60 to 150° C. in the presence of water a starch material heat-treated using steam at 100 to 130° C. under a reduced pressure and swelling the starch particles of the starch material, and steps of subsequently drying the swollen starch particles and obtaining a mixture comprising the starch particle, and amylose and amylopectin present outside the starch particle. However, in Examples in which the above steps were carried out, the heat treatments were performed in the presence of water at a temperature of 95 to 120° C., exceeding 90° C., and the production method of this document is different from that of the present invention in the aspect of, i.e., the temperature for heating in the presence of water at the step after a starch slurry is prepared. In this PATENT DOCUMENT, as a result of the heat treatment at a temperature exceeding 90° C., the outer shell structure derived from raw starch is destructed as described to read amylose and amylopectin present outside the starch particle, and the water soluble components are contained in an amount of 10% by weight or more preventing water from permeating into a solid preparation, whereby a sufficient disintegrating force was not achieved (see Comparative Example 4 of the present application).

PATENT DOCUMENT 17 describes a method for producing a tablet which is characterized by comprising molding a tablet by a compression molding method using, as a powder binder, rice starch and/or a rice starch derivative having a water content of 6 to 14% mass. It is described that the rice starch of this PATENT DOCUMENT has the primary particle with an average particle diameter of 4.8 μm in the dry state, and hence it is different from the present invention which has the primary article of 25 to 80 μm. Further, the production method of this document is also different from that of the present invention in the respect that there is no step of preparing a starch slurry or heating the starch slurry as described that the heat treatment was carried out for at least 30 minutes at a temperature of 75° C. or higher, followed by adjusting water content thereof.

PATENT DOCUMENT 18 describes a method for producing a granulated composition which is characterized by comprising wet granulating particulates containing one or more active ingredients having a solubility in water of 0.0001 to 10 g/L using, as a binder, a functional starch powder having a water retention capacity of 400% or higher, a gel indentation load of 100 to 3000 g, containing 40 to 95% of water soluble components. PATENT DOCUMENT 19 describes a method for producing a granulated composition which is characterized by comprising wet granulating particulates containing one or more active ingredients using, as a binder, a functional starch powder having a water retention capacity of 400% or higher, containing 40 to 95% by weight of water soluble components, having a gel indentation load of 100 g or more and less than 200 g. These PATENT DOCUMENTS are different from the present invention in the aspect of the amount range of the water soluble component. The water soluble component is described to be a value expressing the amount of the paste component which was gelatinized and become water soluble by heat treatment of the starch powder, namely the starch powder has 40 to 95% by weight of itself been gelatinized and is also different in the particle structure from the processed starch of the present invention which has the outer shell structure derived from raw starch. Further, these PATENT DOCUMENTS describe a production method comprising steps of further heating at 60 to 150° C. in the presence of water a starch material heat-treated using steam at 100 to 130° C. under a reduced pressure and swelling the starch particles of the starch material, and steps of subsequently drying the swollen starch particles and obtaining a powder mixture comprising the starch particle, and amylose and amylopectin present outside the starch particle. However, in Examples in which the above steps were carried out, the heat treatments were performed in the presence of water at a temperature of 95 to 120° C., exceeding 90° C., and the production method of these documents are different from that of the present invention in the aspect of the heat temperature in the presence of water in the step after a starch slurry is prepared. In this PATENT DOCUMENT, as a result of the heat treatment at a temperature exceeding 90° C., the outer shell structure derived from raw starch is destructed as described to read amylose and amylopectin present outside the starch particle, and the water soluble components are contained in an amount of 10% by weight or more preventing water from permeating into a solid preparation, whereby a sufficient disintegrating force was not achieved.

PATENT DOCUMENT 20 describes a solid pharmaceutical preparation containing (a) a drug and (b) 10 to 90% by weight of a pregelatinized starch. In this patent, the drug and the starch are both gelatinized, whereas only the starch is gelatinized in the present invention, where the difference lies.

In addition to the processed starch in which a raw starch is physically modified, the disintegrating properties of starches have been enhanced by chemical treatment using a crosslinking agent, or the like, as shown in PATENT DOCUMENTS 21 to 28.

PATENT DOCUMENT 10 describes a rapid swelling starch containing less than 2% by weight of a cold water soluble component (which corresponds to the water soluble component of the present invention) and having a changed crystal structure with a size identical with or smaller than natural starch. The processed starch of the present invention has a different amount range of the water soluble components from the rapid swelling starch. The processed starch of the present invention has an average particle size of the primary particles of 25 to 80 μm in the dry state, larger than a natural starch material, and is different from the starch of PATENT DOCUMENT 10 in the aspect of having an average particle size larger than a natural starch. Further, the PATENT DOCUMENT describes that when the rapid swelling starch is observed using a microscope in the dry state, the polarized cross somewhat irregular and different from that of a natural particulate but extremely distinct is found. This is different in the aspect of the particle structure from the processed starch of the present invention which is nonbirefringent particles. Furthermore, it is described that a part of the starch crystallinity needs to be inhibited before the removal/destruction treatment to obtain the rapid swelling starch of this patent. The inhibition means a treatment by a chemically modified reagent such as an organic solvent or an inhibitor which makes it different from the present invention in the aspect of involving the chemical treatment.

PATENT DOCUMENT 21 discloses a disintegrant containing as a main ingredient a low swelling starch powder which is crosslinked and pregelatinized, PATENT DOCUMENT 22 discloses a crosslinked pregelatinized starch, PATENT DOCUMENT 23 discloses a crosslinked amylose, PATENT DOCUMENT 24 discloses a starch which is hydrolyzed with an acid or an enzyme, PATENT DOCUMENT 25 discloses starch ether, PATENT DOCUMENT 26 discloses an enzymatically treated glucose polymer, PATENT DOCUMENT 27 discloses an enzymatically decomposed starch, PATENT DOCUMENT 28 discloses a starch obtained by heat dehydration after alkali treatment followed by heat treatment. However, the production methods of these documents require the use of an expensive organic solvent or reagent, alkali, enzyme, or the like, and involve complicated steps, consequently incurring high cost, and the influence by a remained organic solvent or reagent, alkali, enzyme, or the like, caused failure to always provide satisfactory starch in respect of the safety and stability of an active ingredient.

As described above, no prior art currently provides a very commonly eaten, highly safe disintegrant of a natural material origin which has a high disintegrating force even when added in a small amount as well as has a low reactivity to an active ingredient and little hygroscopicity, hence has good preparation storage stability, and further obtained by a method obviating chemical treatment. Such a disintegrant has been in demand.

PATENT DOCUMENT 1: JP 58-32828 A
PATENT DOCUMENT 2: U.S. Pat. No. 5,164,014
PATENT DOCUMENT 3: JP 62-7201 B
PATENT DOCUMENT 4: JP 53-5725 B
PATENT DOCUMENT 5: JP 58-27774 B
PATENT DOCUMENT 6: JP 59-47600 B (U.S. Pat. No. 4,447,601)
PATENT DOCUMENT 7: Japanese Patent No. 3004758
PATENT DOCUMENT 8: JP 56-11689 B
PATENT DOCUMENT 9: JP 2006-45222 A
PATENT DOCUMENT 10: JP 2004-238622 A
PATENT DOCUMENT 11: JP 11-269202 A (U.S. Pat. No. 6,143,324)
PATENT DOCUMENT 12: JP 2001-39894 A
PATENT DOCUMENT 13: U.S. Pat. No. 4,072,535
PATENT DOCUMENT 14: U.S. Pat. No. 3,622,677 (JP 46-21471 A)
PATENT DOCUMENT 15: JP 48-68726 A
PATENT DOCUMENT 16: WO2005/005484
PATENT DOCUMENT 17: JP 2006-176496 A
PATENT DOCUMENT 18: JP 2007-001875 A
PATENT DOCUMENT 19: JP 2007-001999 A
PATENT DOCUMENT 20: JP 2006-001924 A
PATENT DOCUMENT 21: JP 63-7531 B
PATENT DOCUMENT 22: U.S. Pat. No. 4,369,308
PATENT DOCUMENT 23: JP 8-507769 A
PATENT DOCUMENT 24: U.S. Pat. No. 455,177
PATENT DOCUMENT 25: JP 52-66619 A
PATENT DOCUMENT 26: JP 2005-213496 A
PATENT DOCUMENT 27: JP 2004-137230 A
PATENT DOCUMENT 28: WO1996/022110

DISCLOSURE OF THE INVENTION

Problems to be Solved by the Invention

An object of the present invention is to provide, under the circumstances described above, a commonly eaten, highly safe disintegrant of a natural material origin which has a high disintegrating force even when added in a small amount as well as a low reactivity to an active ingredient and little hygroscopicity, hence has good preparation storage stability, and further is obtained by a method obviating chemical treatment.

Means for Solving the Problems

The present inventors conducted extensive studies on the crystallinity, swelling properties, water retention capacity, gelatinization properties of starch powders. As a result, the inventors found that the suitable properties which solve the above problems can be imparted by depriving the crystallinity to the extent that the outer shell structure of starch powder is not destroyed and enhancing the water retention capacity and swelling properties of starch to the maximum level, whereby the present invention has been accomplished based on these findings.

More specifically, the present invention is as follows.

(1) A processed starch powder having a water soluble component amount of more than 2% by weight and less than 10% by weight and a water retention capacity of more than 600% and 1500% or less, and being a nonbirefringent particle.

(2) The processed starch powder according to item (1), wherein an average particle size of primary particles is 25 to 80 μm in a dry state and an average particle size of primary particles is 45 to 160 μm in a swollen state in water.

(3) The processed starch powder according to item (1) or (2) which has an outer shell structure derived from a raw starch grain.

(4) The processed starch powder according to any one of items (1) to (3), which is obtained without chemically treating a natural starch material having an amylose content of 20% by weight or more and less than 30% by weight.

(5) The processed starch powder according to any one of items (1) to (4), wherein the average particle size of primary particles of dry particles is larger than that of a natural starch material.

(6) The processed starch powder according to any one of items (1) to (5), wherein the natural starch material is a potato starch.

(7) The processed starch powder according to any one of items (1) to (6), which is obtained by a process comprising the steps of (i) heat-treating a natural starch material using steam at 100 to 130° C. under reduced pressure conditions, (ii) preparing the heat-treated starch material into a starch slurry having a solid content of 1 to 20% by weight, (iii) heat-treating the starch slurry in a temperature range from more than a temperature of 10° C. higher than a gelatinization onset temperature intrinsic to starch to less than 90° C., and (iv) subsequently, drying the heat-treated starch slurry.

(8) The processed starch powder according to any one of items (1) to (7), wherein a sedimentation volume is 7 cm$^3$/g or more and 20 cm$^3$/g or less.

(9) The processed starch powder according to any one of items (1) to (8), wherein a swelling ratio of the primary particles in the dry state to the primary particles in the swollen state in water is 1.5 to 5.0.

(10) The processed starch powder according to any one of items (1) to (9), wherein the processed starch powder is a disintegrant.

(11) A composition comprising the processed starch powder according to any one of items (1) to (10) and one or more active ingredients.

(12) The composition according to item (11) having a hardness of 100±10 N and a disintegration time of 70 seconds or less when obtained by direct compression.

(13) The composition according to item (11) having a hardness of 100±10 N and a disintegration time of 60 seconds or less when obtained by compression after high shear granulation.

(14) The composition according to item (11) having a hardness of 100±10 N and a disintegration time of 130 seconds or less when obtained by compression after fluidized bed granulation.

(15) The composition according to any one of items (11) to (14) comprising 0.2 to 5% by weight of the processed starch powder in the composition.

(16) The composition according to any one of items (11) to (15), wherein the one or more active ingredients are selected from active pharmaceutical ingredients and food ingredients.

(17) A process for manufacturing the processed starch powder according to item 1 or 7, the process comprising the steps of (i) heat-treating a natural starch material using steam at 100 to 130° C. under reduced pressure conditions, (ii) preparing the heat-treated starch material into a starch slurry having a solid content of 1 to 20% by weight, (iii) heat-treating the starch slurry in a temperature range from more than a temperature of 10° C. higher than a gelatinization onset temperature intrinsic to starch to less than 90° C., and (iv) subsequently, drying the heat-treated starch slurry.

Advantages of the Invention

The present invention can provide a very commonly eaten, highly safe disintegrant of a natural material origin which has a high disintegrating force even when added in a small amount as well as a low reactivity to an active ingredient and little hygroscopicity, hence has good preparation storage stability, and is obtained by a method obviating chemical treatment.

More specifically, when the processed starch obtained by the present invention is added in an amount of preferably 1 to 5% by weight to a preparation such as tablets, granules, fine granules, pills and capsules, the disintegration of tablets, granules, and fine granules are enhanced and the release of an active ingredient from these preparations can be improved.

BRIEF DESCRIPTION OF THE DRAWINGS

FIG. 8a is a drawing showing an optical microscope photograph of the particle morphology of processed starch I swollen in water (Comparative Example 5) (not polarized);

BEST MODE FOR CARRYING OUT THE INVENTION

Figure 1:
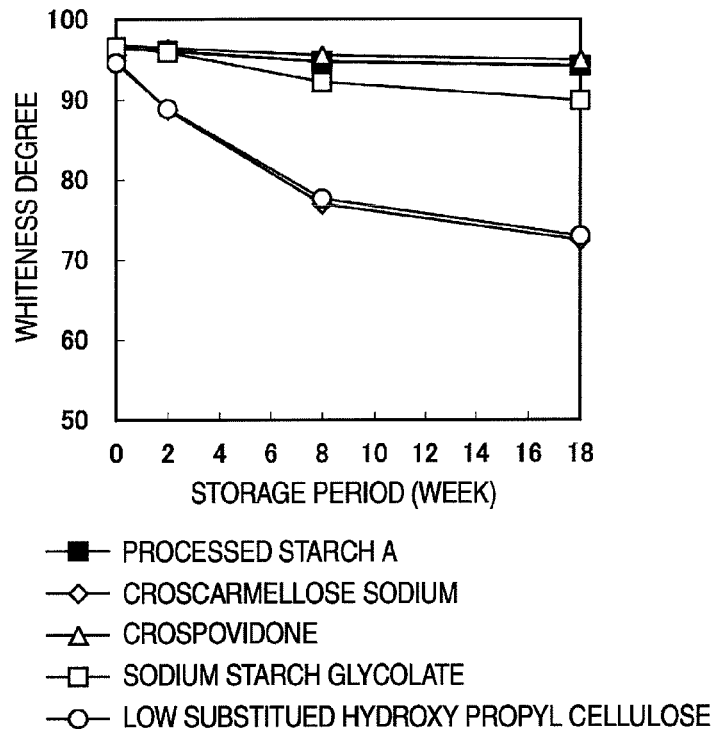
FIG. 1 is a drawing showing the time-dependent changes in the whiteness degree of an aminophylline tablet (Example 6, Comparative Examples 12 to 15)

Hereinafter, the present invention is described in detail.

The processed starch of the present invention needs to contain a water soluble component in the range from more than 2% by weight to less than 10% by weight. An amount of 2.4% by weight or more and 9.7% by weight or less is more preferable, and 3.5% by weight or more and 9% by weight or less is particularly preferable. The amount of the water soluble component is defined as a value obtained by the following calculation. More specifically, a dry weight (g) of a water soluble component is determined by adding 97 g of pure water in the range of 20° C.±5° C. to 3 g of the processed starch, stirring for 2 hours using a magnetic stirrer for dispersion, moving 40 cm$^3$ of the obtained dispersion to a 50 cm$^3$ centrifugation tube to centrifuge for 15 minutes at 5000 G, and putting 30 cm$^3$ of the supernatant to a weighing bottle and drying it at 110° C. to a certain weight. Further, an absolute dry weight (g) of the processed starch is determined by drying 1 g of the processed starch at 110° C. to a certain weight. The amount of the water soluble component is defined as the value determined by these values and the formula (1) below.

Water soluble component amount (% by weight)=(dry weight (g)×100÷30)÷absolute dry weight (g) of 1 g of processed starch×100　　(1)

The value calculated using the above formula almost remained unchanged even when the stirring time by a magnetic stirrer was changed to 10 minutes and the centrifugal force was changed to 2000 G.

The amount of the water soluble component is a value expressing the amount of the paste component which has been gelatinized and has become water soluble by the heat treatment of the starch powder. The water soluble component expresses strong adhesiveness when dissolved in water. The water soluble component is preferably contained in a small amount because it forms an adhesive film on the surface or in the pore of a solid preparation which inhibits the water permeation into the solid preparation. It is preferable to make an amount of the water soluble component less than 10% by weight so that the inhibition of water permeation into a solid preparation can be minimized and good disintegrating properties are assured. The smaller the amount of the water soluble component, the better since the inhibition of water permeation into a solid preparation can be prevented. However, since the crystallinity of the starch particle needs to be partially deprived to give a determined range of the swelling ratio for assuring the swelling properties of the starch particle, the generation of water soluble components caused by the deprivation of the crystallinity is not completely evitable, hence making the lower limit amount of the water soluble component is about 2% by weight at best.

Further, the processed starch of the present invention must have a water retention capacity of more than 600% and 1500% or less. A capacity of more than 600% and 1300% or less is more preferable, and more than 600% and 1200% or less is particularly preferable. The water retention capacity herein is defined by the value determined using the following formula (2). The processed dry starch W0 (g) (about 1 g) is gradually placed to a 50 cm$^3$ centrifuge tube in which about 15 cm$^3$ of pure water in a temperature range of 20° C.±5° C. has been placed and dispersed in the pure water until the mixture becomes clear to translucence while stirring for about 2 minutes using a spatula. The pure water in a temperature range of 20° C.±5° C. is further added so that the mixture fills up about 70% of a 50 cm$^3$ sedimentation tube and centrifugation is carried out (2000 G, 10 min). Within 1 minute after the completion of the centrifugation, the separated upper layer is cut off and a water retention capacity is determined based on the weight W (g) remained in the lower layer (starch+pure water amount retained in the starch) using the following formula (2).

$$\text{Water retention capacity (\%)} = 100 \times (W - W0)/W0 \qquad (2)$$

When a water retention capacity is less than 600%, the starch particle cannot take up enough water and fails to swell up largely, whereby sufficient disintegrating properties cannot be achieved, hence not preferable. When a water retention capacity exceeds 1500%, the starch particle swells up too much, likely forming a highly viscous gel due to the engagement of the swollen starch particles, or the like, and the water permeation into a solid preparation is consequently inhibited, whereby sufficient disintegrating properties cannot be achieved, hence not preferable.

Furthermore, the processed starch powder of the present invention must be a nonbirefringent particle. The nonbirefringent particle used in the present invention refers to starch particles 90% or more of which in terms of the particle number in the swollen state in water do not exhibit a birefringent property when the starch particles are observed by a polarizing microscope. The starch particle of the present invention is, due to its looser crystallinity compared with natural starch, characterized in that starch particles showing a distinct polarized cross are extremely few, i.e., less than 10% in terms of the particle number. The nonbirefringent processed starch has a potential of largely swelling by the hydration of the amylose and amylopectin particles composing the starch particles with water. When 10% or more of birefringent starch particles are contained in terms of the particle number, the amylose and amylopectin composing the starch are strongly bonded by the intermolecular hydrogen bond and hence cannot be freely hydrated with water, thereby failing to swell largely. As a result, when attempting to impart sufficient disintegrating properties, a large amount is required which consequently limits the amount of an active ingredient to be added, hence not preferable. The nonfirefringent processed starch particle of the present invention is different from the processed starches by the following conventional art. More specifically, the processed starch particle of the present invention is different from the processed starch powder of PATENT DOCUMENTS 2 to 5 which is composed largely of β-starch or natural starch, the processed starch powder of PATENT DOCUMENT 8 which is a modified starch wherein a part of the particles are destroyed by the downsizing and the distinct polarized cross as seen in raw cornstarch is found, the processed starch of PATENT DOCUMENT 9 in which most of the particles are formed by the continuous engagement of a birefringent part and a mechanically modified nonbirefringent part, the processed starch powder of PATENT DOCUMENT 10 exhibiting the polarized cross which is somewhat irregular and different from that of a natural particulate but extremely distinct when observed using a microscope in the dry state, the processed starch powders of PATENT DOCUMENTS 11 and 12 which contains the non-swelling birefringent particles in a proportion of one sixth or more, and the processed starches of PATENT DOCUMENTS 13 and 14 in which the particles are partially crushed due to the downsizing and the distinct polarized cross is found as in raw cornstarch. More preferably, the particle of processed starch powder is practically nonbirefringent.

The processed starch of the present invention has an average particle size of the primary particles in the dry state of preferably 25 μm or more and 80 μm or less. An average particle size of the primary particles in the dry state is further preferably 28 μm or more and 70 μm or less, and particularly preferably 32 μm or more and 60 μm or less. The average particle size of the primary particles in the dry state is defined as a value calculated by the following measurement. More specifically, an optical microscope image of the processed starch powder is processed by image analysis treatment (manufactured by InterQuest, Co., Ltd., processor: Hyper 700, software: Imagehyper), and the long side of a rectangle with the smallest area among the rectangles circumscribing a particle is determined as the primary particle size of the particle. The average particle size of the primary particles in the dry state is an average of at least 400 particles. An average particle size of the primary particles of 25 μm or more is preferable because the starch particle which absorbs water and swells in a solid preparation applies a great stress to other surrounding ingredients including an active ingredient, and thus a strong disintegrating force can be attained. The larger an average particle size of the primary particles, the more preferable in viewpoint of the disintegrating force, however, the size which maintains the conditions under which the outer shell structure of the starch particle is not destroyed is up to about 80 μm. Moreover, the processed starch of the present invention preferably has an average particle size of the primary particles in the dry state larger than that of a natural starch material. The processed starch of the present invention is characterized by swelling the particles maximally within the extent such that the outer shell structure of the starch particle of a natural starch material is not destroyed, and the average particle size of the primary particles in the dry state of the processed starch of the present invention becomes larger than the average particle size of the primary particles of a natural starch material in the dry state.

Further, the processed starch of the present invention has an average particle size of the primary particles in the swollen status in water of preferably 45 μm or more and 160 μm or less. An average particle size of the primary particles in the swollen status in water is preferably 60 μm or more and 110 μm or less, and particularly preferably 64 μm or more and 110 μm or less. The average particle size of the primary particles in the swollen state in water is defined as a value calculated by the measurement below. More specifically, 200 g of pure water in a temperature range of 20° C.±5° C. is put in a container, 1.0 g of the processed starch is added over the period of 2 minutes while stirring using a magnetic stirrer at 500 rpm, and is dispersed for 3 minutes after the addition. The obtained dispersion is ultrasonically treated for 5 minutes and a part of the dispersion is observed using an optical microscope. The observation is carried out under a magnification such that 20 particles or more are present in the sight, and the maximum sizes of all distinguishable primary particles are measured. The measurements of the maximum size are repeated five times, and an average value of the maximum sizes of all particles from the five-times measurement is determined to be the average particle size of the primary particles in the swollen state. When a starch particle has an average particle size of the primary particles in the swollen state in water is 45 μm or more, the stress generated when the starch particle swells destructs a solid preparation and the content is likely to be released, hence preferable. The larger an average particle size of the primary particles in the swollen state in water, the greater the swelling force becomes when the starch absorbs water, and thus a force for destroying a solid preparation becomes intense, hence preferable. On the other hand, when a swollen particle is too large, the swollen starch particles are engaged with each other and form a highly viscous gel, thereby blocking the water absorption into a solid preparation and prolonging the disintegration time, hence not preferable. The size which maintains the condition under which the outer shell structure of the starch particle is not destroyed is up to about 160 μm. The processed starch powder of the present invention preferably has a swelling ratio of the primary particles in the dry state to the primary particles in the swollen state in water of 1.5 or more and 5.0 or less. The swelling ratio is more preferably 1.7 or more and 4.0 or less, and particularly preferably 1.8 or more and 3.0 or less. The swelling ratio of the primary particles in the dry state to the primary particles in the swollen state in water is defined by a value determined by the following formula (3) based on the average particle size (W1) (μm) of the primary particles in the dry state and the average particle size W2 (μm) of the primary particles in the swollen state determined above.

$$\text{Swelling ratio of primary particles in dry state to primary particles in swollen state in water} = W2\,(\mu m)/W1\,(\mu m) \quad (3)$$

When a swelling ratio of the primary particles in the dry state to the primary particles in the swollen state in water is 1.5 times or more, an enormous swelling force is generated when the starch powder absorbs water and sufficient disintegrating force for destroying a solid preparation to release the content can be provided. The greater the swelling ratio of the primary particles in the dry state to the primary particles in the swollen state in water is, the greater the swelling force becomes when the starch powder absorbs water causing the disintegrating force for destroying a solid preparation to be more intense, hence preferable. However, when a swelling ratio is too great, the swollen starch particles are engaged with each other and form a highly viscous gel, thereby blocking the water absorption into a solid preparation and prolonging the disintegration time, hence not preferable. A swelling ratio is preferably 5.0 or less since good disintegrating properties can be assured.

The shape of the particles composing the processed starch of the present invention preferably has the outer shell structure derived from a raw starch grain. Having the outer shell structure herein means that 90% or more of the starch particles in terms of the particle number maintain the shape derived from a natural starch when observed using an optical microscope. It is preferable that the starch particle preserves the shape of the primary particles, the same constituent unit as raw starch when swollen in water, and individual primary particle remains distinguishable. When the starch particle is not destroyed and the outer structure is preserved intact, the force which the starch particle absorbing water and swelling in a solid preparation, applies to the other surrounding ingredients including an active ingredient is not affected, whereby a strong disintegrating force accompanying the swelling of starch particle is attained. The starch particle, in which an individual primary particle derived from raw starch is destroyed to the extent of not being distinguishable, irreversibly swells in water. Further, since the gluey water soluble components such as amylose and amylopectin elute to the outside the particle, a highly viscous gel is formed, and the water absorption into a solid preparation is blocked, hence not preferable.

The processed starch of the present invention is preferably a processed starch powder obtained without chemically treating a natural starch material having an amylose content of 20% by weight or more and less than 30% by weight. Denpun Kagaku Handbook ("Starch Chemistry Handbook" in Japanese) (supervised by Jiro Nikuni, Asakura Publishing Co., Ltd., 1977, p. 160) describes that the ratio of amylose to amylopectin in the starch is specific to the plant type and organ in which the starch is synthesized and most of the typical starches have an amylose content of 20 to 25% by weight. It is also described that a cornstarch having an amylose content of 0 to 80% by weight using a mutant strain in known, but the starch produced by genetic engineering is not preferable as the processed starch of the present invention in the aspect of safety as a food product. Further, it is described (p. 300) that waxy cornstarch, and the like, is the starch obtained from waxy strain which composes of 100% of amylopectin and theoretically does not contain amylose, and thus, such a starch is not preferable as a natural starch material for the processed starch of the present invention.

Examples of the natural starch material containing 20% by weight or more and less than 30% by weight of amylose include uruchi rice (about 17% by weight of amylose), maize (about 25% by weight), potato (about 25% by weight), sweet potato (about 19% by weight), tapioca (about 17% by weight) and greenpea (about 25% by weight). The plant type is not limited insofar as a natural starch material has an amylose content of 20% by weight or more and less than 30% by weight, but the potato is preferable in view of high swelling properties of the particle and consequently easy control of a high water retention capacity. The natural starch material may be used singly from the above or in combination of two or more.

The chemical treatment mentioned in the present invention refers to treatment, or the like, involving the use of an organic solvent, the use of an inhibitor such as propylene oxide, phosphorus oxychloride, or the like, the use of a crosslinking agent, the use of an acid or alkali, the use of an enzyme, and the treatment or the like with chemical reactions such as etherification, alkylation, and esterification. The processed starch of the present invention is imparted with suitable water absorbing property and swelling properties without these treatments but by only physical treatments such as treating the starch powder using steam under a reduced pressure, heat-treating it in the presence of water and drying, and the like.

The processed starch of the present invention has a sedimentation volume of preferably 7 cm$^3$/g or more and 20 cm$^3$/g or less. A sedimentation volume is further preferably 9.1 cm$^3$/g or more and 18 cm$^3$/g or less, and particularly preferably 9.5 cm$^3$/g or more and 18 cm$^3$/g or less. The sedimentation volume of the processed starch is defined as a value determined by dispersing 1.0 g of the processed starch in pure water in a temperature range of 20±5° C., moving the dispersion to a 100 cm$^3$ sedimentation tube to give a total amount of 100 cm$^3$, allowing the dispersion to stand for 16 hours, and then measuring a volume V (cm$^3$) of the bottom layer among the separated top and bottom layers and an absolute dry weight (g) of the 1.0 g processed starch (the value calculated in the same manner as in the above formula (2)) using the following formula (4).

Sedimentation volume (cm$^3$/g)=$V$ (cm$^3$)/absolute dry weight ($g$) of 1.0 g processed starch    (4)

A sedimentation volume of the processed starch of less than 7 cm$^3$/g provides insufficient swelling force when the starch particle absorbs water, and imparts only poor disintegrating properties to a solid preparation, hence not preferable. On the other hand, when a sedimentation volume of the processed starch is more than 20 cm$^3$/g, the swollen starch particles are engaged with each other and form a highly viscous gel, thereby blocking the water absorption into a solid preparation and prolonging the disintegration time, hence not preferable. When a sedimentation volume of the processed starch is in a range from 7 cm$^3$/g or more to 20 cm$^3$/g or less, the disintegration of a solid preparation is enhanced, hence preferable.

The processed starch of the present invention preferably has an angle of repose of 45° or less. An angle of repose is further preferably 43° or less, and particularly preferably 42° or less. Further, the processed starch of the present invention preferably has a bulk density in the range from 0.1 to 0.7 g/cm$^3$ or less. A bulk density is further preferably 0.20 to 0.50 g/cm$^3$, and particularly preferably 0.25 to 0.45 g/cm$^3$. A specific processed starch having an angle of repose of 45° or less as well as a bulk density in the range of 0.1 to 0.7 g/cm$^3$ has good mixing and dispersing properties with an active ingredient and other additives and is dispersed uniformly in a solid preparation, hence preferable.

Hereinafter, methods for producing the processed starch of the present invention are described.

The processed starch of the present invention can be obtained by a step of heat-treating a natural starch material using steam at 100 to 130° C. under reduced pressure conditions, a step of preparing the heat-treated starch material into a starch slurry having a solid content of 1 to 20% by weight, a step of heat-treating the starch slurry at a temperature in a range from a temperature of 10° C. higher than a gelatinization onset temperature intrinsic to starch to less than 90° C., and subsequently a step of drying the heat-treated starch slurry.

Examples of the starch material usable in the production include natural starches such as rice, maize, potato, sweet potato, tapioca, and green pea. The natural starch material is not limited insofar as it contains a starch substance, but the potato is preferable in view of high swelling properties of the particle and consequently easy control of a high water retention capacity. The starch material may be used singly from the above or may be used in mixture of two or more. Further, the large particle size of the starch material is more preferable in view of easy swelling.

When a natural starch material without further treatment is heated at a temperature equal to or higher than the gelatinization onset temperature intrinsic to the natural starch, the outer shell structure derived from the starch grain is destroyed. For this reason, it is required, before the preparation of the starch slurry, to heat-treat the natural starch material using steam at 100 to 130° C. under a reduced pressure as described in e.g., JP 4-130102 A and JP 7-25902 A.

For example, JP 4-130102 A discloses (1) a moist-heat treatment process in which starch is heated for a determined period of time and cooled by placing the starch in a hermetically sealable container equipped with both a decompression line and a pressurized steam line and resistant to an internal pressure and an external pressure, the pressure is reduced and pressurized heating by introducing steam is carried out, or by repeating the procedure, (2) in addition to the process of (1), a moist-heat treatment process for producing a starch whose particle is swollen but does not practically exhibit viscosity and has extremely high α-amylase adsorbability when a water suspension is heated at an inside-can temperature of at least 120° C. or higher, (3) in addition to the process of (1) or (2), a moist-heat treatment process in which the compression is reduced after heating, followed by cooling. Any of these moist-heat treatment processes may be employed.

Further, JP 7-25902 A discloses (4) a process for producing moist-heat treated starch grains obtained by moist-heat treating a starch grain, comprising the process repeating at least once the first step of decompressing the starch grain filled in a pressure resistant container and the second step of heating and compressing by introducing steam after the decompression, (5) a production process in which, in the second step of the production process (4), the heating is carried out at 80° C. or higher for 5 minutes to 5 hours. Any of these processes may be employed.

Using these processes, the starch obtained by heat-treating a natural starch material using steam under a reduced pressure has the particle which is hollow inside and has the outer shell part with an increased crystallinity. Such a starch has characteristics in that the polarized cross pattern observed on a polarized image taken by an optical microscope is more ambiguous than raw starch and birefringent particles are decreased. Further, the hollow part is thought to be structured by amylose and amylopectin in the loosen crystal state where the digestibility by α-amylase is more increased than raw starch.

The method for preparing the starch slurry is not limited and any known methods can be employed. The temperature for preparing the starch slurry is preferably a temperature of 10° C. lower than the gelatinization onset temperature of a starch material. Within such a temperature range, the starch gelatinization is prevented in the step of preparing the starch slurry, making it easier to control the gelatinization in the subsequent step of heating the starch slurry. Further, the solid content of the starch slurry must be 1 to 20% by weight or lower. A solid content of less than 1% by weight makes the productivity low, hence not preferable. Further, a solid content exceeding 20% by weight causes uneven heating, failing to assure constant quality, hence not preferable.

The starch slurry after being subjected to the moist-heat treatment preferably has a value of 400 brabender unit (BU) or less when adjusted to a concentration of 5% by weight as well as a maximum viscosity of 1000 BU or less when maintained at 95° C. for 30 minutes.

The method for heating the starch slurry is not limited and any known methods can be applied. For example, they include a method in which the starch slurry in the presence of water is put in a jacketed reactor and steam is introduced to the jacket for heating, a method in which steam is mixed with the starch slurry in the presence of water, a method in which the starch slurry is heated in a liquid reservoir of a drum dryer and a method in which gelatinization and spraying are carried out simultaneously while steam is supplied to a starch slurry at the time of spray drying, and the like. The method in which steam is mixed with the starch slurry in the presence of water is preferable in viewpoint of the heating time of the starch particle. The heating temperature is preferably, in terms of the liquid temperature after gelatinizing the starch by the above various methods, in the temperature range from more than a temperature of 10° C. higher than the gelatinization onset temperature intrinsic to starch to less than 90° C. The heating temperature is more preferably in the temperature range from more than a temperature of 12° C. higher than the gelatinization onset temperature intrinsic to starch to less than 87° C., and particularly preferably in the temperature range from more than a temperature of 13° C. higher than the gelatinization onset temperature intrinsic to starch to less than 86° C. When a heating temperature is lower than a temperature of 10° C. higher than the gelatinization onset temperature, the starch particle does not swell largely, thereby producing the starch powder with poor swelling properties, hence not preferable. When a heating temperature is 90° C. or higher, the starch particle swells too large, thereby causing the breakage of the outer shell structure, hence not preferable. In a heating temperature within the temperature range from a temperature of 10° C. higher than the gelatinization onset temperature to less than 90° C., the starch particle can be swollen largely without the outer shell structure being broken, hence preferable.

In this regard, according to Denpun Kagaku Handbook ("Starch Chemistry Handbook" in Japanese) (supervised by Jiro Nikuni, Asakura Publishing Co., Ltd., 1977, p. 36), the gelatinization onset temperatures of major starches by photopastegraphy are 61.0° C. for potato, 66.8° C. for corn, 65.4° C. for tapioca and 65.8° C. for sweet potato. One of the preferable embodiments of the processed starch powder of the present invention is to use potato starch as a natural starch material. Since the gelatinization onset temperature of potato starch is 61.0° C. as described above, when using potato starch as a raw material, the heating temperature after the preparation of the starch slurry ranges preferably from a temperature exceeding 71° C. to less than 90° C., further preferably 73° C. or higher to 87° C. or lower, particularly preferably 74° C. or higher to 86° C. or lower. When cornstarch is used as a raw material, the heating temperature after the preparation of the starch slurry ranges preferably from a temperature exceeding 76.8° C. to less than 90° C., further preferably 77° C. or higher to 87° C. or lower, particularly preferably 78° C. or higher to 86° C. or lower. When tapioca starch is used as a raw material, the heating temperature after the preparation of the starch slurry ranges preferably from a temperature exceeding 75.4° C. to less than 90° C., further preferably 76° C. or higher to 87° C. or lower, particularly preferably 77° C. or higher to 86° C. or lower. When sweet potato starch is used as a raw material, the heating temperature after the preparation of the starch slurry ranges preferably from a temperature exceeding 75.8° C. to less than 90° C., further preferably 76° C. or higher and 87° C. or lower, particularly preferably 77° C. or higher and 86° C. or lower.

The drying method is not limited, and examples include freeze drying, spray drying, drum drying, tray drying, air-stream drying and vacuum drying. Spray drying and drum drying are industrially preferable.

Further, the processed starch of the present invention has a bulk density ranging preferably from 0.1 or more to 0.7 g/cm$^3$ or less. The bulk density is affected by the level of liquid concentration at the drying step and also affected by the rotation number of an atomizer at the spray drying step. Thus, these factors may be adjusted as necessary to have the bulk density within the above preferable range.

Starches which are mainly used in pharmaceuticals and free of chemical treatment are partly pregelatinized starch and pregelatinized starch which are obtained by heating a natural starch for the gelatinization followed by drying. The partly pregelatinized starch has starch grains partially swollen without the breakage thereof by carrying out heat treatment at 50° C. or higher to a temperature of about 10° C. higher than the intrinsic gelatinization onset temperature or lower, or at a temperature substantially not higher than the gelatinization temperature as described in Japanese Patent No. 3004758 and JP 11-269202 A. However, since the heating temperature is low in these treatments, the swelling properties cannot be much enhanced by loosening the crystallinity of the starch particle, failing to express an intense disintegrating force. Alternatively, in the potato starch having a wide range of the particle size distribution and hence having greatly diverse gelatinization onset temperatures depending on the particle size, non-swelling particles in which the gelatinization does not progress and broken particles caused by too much swelling form a mixture which fails to express an intense disintegrating force. In this regard, according to Denpun Kagaku Handbook ("Starch Chemistry Handbook" in Japanese) (supervised by Jiro Nikuni, Asakura Publishing Co., Ltd., 1977, p. 36), the gelatinization onset temperatures of major starches by photopastegraphy are 60.0° C. for large size potato starch, 61.4° C. for middle size potato starch and 63.4° C. for small size potato starch, and the gelatinization onset temperature largely varies depending on the particle size (see Comparative Examples 7 and 8 of the present application). Other partly pregelatinized starches, as described in PATENT DOCUMENTS 16, 18 and 19, have 10 to 90% by weight of amylose and amylopectin (corresponding to the water soluble components of the present invention) eluted outside the starch particle as a result of heat-treating a starch material using steam at 100 to 130° C. under a reduced pressure, followed by further heat treatment at 60 to 150° C. in the presence of water. However, the starch powder, which is heated at a temperature so high that 10 to 90% by weight of the water soluble components are eluted outside the starch particle (heated in a temperature range from 95 to 120° C. in Example of WO2005/5484) and most of which have broken outer shell structure and thus contains a large amount of water soluble components, has little stress applied to the surroundings by the swelling. In addition, the water soluble components form a viscous film on the surface or in the pore of a solid preparation. Accordingly, the disintegration of a solid preparation cannot be promoted (see Comparative Example 5 in the present application). Further, as described in JP 2006-45222 A and JP 46-21471 B, the birefringent starch and nonbirefringent starch form a mixture by applying a mechanical force to the starch powder. However, these starch powders have the outer structures partially destructed due to the mechanical force. For this reason, the particle irreversibly swells in water, and thus, the liquid viscosity is consequently increased, inhibiting the water permeation into a solid preparation whereby a sufficient disintegrating force cannot be achieved (see Comparative Example 9 in the present invention).

The pregelatinized starch is produced by a method in which drum drying is carried out at around 150° C. or a method in which an extrusion is carried out using an extruder at 120 to 160° C. under a high pressure. In the pregelatinized starch obtained by such a method, the heating temperature is so high that the particles swell too much and the most of outer shell structures are destructed, whereby amylose and amylopectin becoming water soluble elute outside the particles. The effluent dries and partially turns to β-starch (crystallization) and become flaky or clumpy particles which are different from the outer shell structure the starch particles inherently have. Thus, the starch powder, in which most of the outer shell structures are destructed by too much gelatinization and hence a large amount of water soluble components are contained, has little stress applied to the surroundings by the swelling. In addition, the water soluble components consequently form a viscous film on the surface or in the pore of a solid preparation. Accordingly, the disintegration of a solid preparation cannot be enhanced, hence not preferable.

The processed starch of the present invention can be obtained by heat-treating a natural starch material using steam at 100 to 130° C. under a reduced pressure, preparing the heat-treated natural starch material into a starch slurry having a solid content of 1 to 20% by weight, then heat-treating the starch slurry in a temperature range from a temperature of 10° C. higher than the gelatinization onset temperature intrinsic to starch to less than 90° C., and subsequently drying, however, the processed starch obtained by such a production process is unexpectedly found to have an intense disintegrating force which have never been found in the conventional partly pregelatinized starch or pregelatinized starch.

The processed starch powder of the present invention has good water retention capacity and is capable of largely swelling, and has a high hardness due to the outer shell structure maintained in the process of swelling in water, thereby applying an enormous outer stress to the starch particles when absorbing water and swelling. On the other hand, since the water soluble components are contained in a small amount, there is not the case that a highly viscous liquid is produced on the surface and in the pore of a solid preparation and the water permeation into the solid preparation is blocked. Owing to the above properties, the processed starch powder of the present invention expresses an intense disintegrating force never found in the conventional partly pregelatinized starch or pregelatinized starch.

The composition comprising the processed starch powder and one or more active ingredients used in the present invention are not limited in the shape as long as they are used in the purpose of quickly releasing the active ingredient in the field of such as medicine, agricultural chemical, fertilizer, feed, food, industry and cosmetics. Examples of the medical purpose include solid preparations such as tablets, powders, fine granules, granules, extracts, pills, and capsules. Tablets are particularly preferable in view of the easy administration and productivity. Lately, a tablet which quickly disintegrates or dissolves within 60 seconds in the mouth, and the processed starch of the present invention is also suitable for such an orally disintegratable tablet. The amount of the processed starch powder of the present invention added to the composition is preferably about 0.1 to 99.9% by weight. An amount of 0.1% by weight or more provides the effects of the processed starch powder of the present invention, whereas an amount of 99.9% by weight or less allows an enough amount of an active ingredient to be added whereby therapeutic effect and efficacy of an active ingredient can be expected. An amount range of using the powder is typically 0.1 to 50% by weight, preferably 0.2 to 10% by weight, particularly preferably 0.2 to 5% by weight.

The active ingredient used in the present invention refers to active pharmaceutical ingredients, agricultural chemical ingredients, fertilizer ingredients, feed ingredients, food ingredients, cosmetics ingredients, pigments, flavors, metals, ceramics, catalysts, surfactants, etc. The active ingredients may be used singly or in combination of two or more. The active ingredient may be used in any form of particle, crystal, oil, liquid, semi-solid, or the like, and may be in any formulation of powder, fine granule, granule, or the like. Further, the active ingredient may be the one coated in the purpose of controlling elution, masking bitter flavor, or the like. The active ingredient may be used singly or in combination of two or more. The active pharmaceutical ingredient, which has strict performance requirement to quick release properties, is the most preferable as the active ingredient.

Further, the composition comprising the processed starch powder of the present invention and one or more active ingredients preferably has a hardness of 100±10 N and a disintegration time of 70 seconds or less when obtained by direct compression. The direct compression used in the present invention refers to the process of uniformly mixing the processed starch of the present invention, ethenzamide (manufactured by API Corporation), a microcrystalline cellulose ("CEOLUS" (registered trade name) KG-802, manufactured by Asahi Kasei Chemicals Corporation), lactose granule (Super-Tab (trade name), manufactured by Asahi Kasei Chemicals Corporation) and a light anhydrous silicic acid (Aerosil 200 (trade name), Nippon Aerosil Co., Ltd.) so as to give a weight ratio of 3/30/10/57/1, subsequently adding magnesium stearate (vegetable magnesium stearate, Taihei Chemical Industry Co., Ltd.) to the mixed particles so as to give a weight ratio of 100/0.5, and slowly mixing to formulate a tablet having a diameter of 8.0 mm and a weight of 0.18 g using a rotary tablet press (Clean Press Collect 12HUK (trade name)/manufactured by Kikusui Seisakusho Co., Ltd.). The compression at the time of tableting is adjusted as necessary to give a hardness of 100±10 N after tableting.

Furthermore, the composition comprising the processed starch powder of the present invention and one or more active ingredients preferably has a hardness of 100±10 N and a disintegration time of 60 seconds or less when obtained by compression after high shear granulation. The compression after high shear granulation used in the present invention refers to the process of uniformly mixing the processed starch of the present invention, ethenzamide (manufactured by API Corporation), a microcrystalline cellulose ("CEOLUS" (registered trade name) PH-101, manufactured by Asahi Kasei Chemicals Corporation) and lactose granule (200 mesh lactose, manufactured by DMV International) so as to give a weight ratio of 3/30/10/57, wet-granulating the mixture in a high shear granulation machine (VG-10, manufactured by Powrex Corp.) using an 8% HPC-L (manufactured by NIPPON SODA CO., LTD.) as a binder under the conditions of a blade rotation number of 210 rpm, a cross chopper rotation number of 2000 rpm, drying the obtained granules at 60° C. for 16 hours, subsequently removing coarse particles using a sieve having an opening of 1400 μm to obtain granules for the compression, and slowly mixing for 30 seconds the obtained granules for the compression with magnesium stearate (vegetable magnesium stearate, Taihei Chemical Industry Co., Ltd.) so as to give a weight ratio of 100/0.5 (the granules/magnesium stearate) to formulate a tablet having a diameter of 8.0 mm and a weight of 0.18 g using a rotary tablet press (Clean Press Collect 12HUK (trade name)/manufactured by Kikusui Seisakusho Co., Ltd.). The compression at the time of tableting is adjusted as necessary to give a hardness of 100±10 N after tableting.

Still furthermore, the composition comprising the processed starch powder of the present invention and one or more active ingredients preferably has a hardness of 100±10 N and a disintegration time of 130 seconds or less when obtained by compression after fluidized bed granulation. The compression after fluidized bed granulation used in the present invention refers to the process of uniformly mixing the processed starch of the present invention, ethenzamide (manufactured by API Corporation), a microcrystalline cellulose ("CEOLUS" (registered trade name) PH-101, manufactured by Asahi Kasei Chemicals Corporation) and crystallized lactose (200 mesh lactose, manufactured by DMV International) so as to give a weight ratio of 1/30/10/59, wet-granulating the mixture in a fluidized bed granulator (MP-01, manufactured by Powrex Corp.) using a 6% HPC-L (manufactured by NIPPON SODA CO., LTD.) as a binder under the condition of drying the mixture until an exhaust-air temperature reaches 40° C. in the spray conditions of, at the fluidized bed top spray and bottom spray, 0.1 MPa, 30 L/min, air flow rate 20 to 40 m$^3$/hr, charge-air temperature 75° C., exhaust-air temperature in due course (28 to 33° C.) and spray solution rate: about 7 g/min, removing coarse particles using a sieve having an opening of 700 μm from the obtained granules to obtain granules for the compression, and slowly mixing for 30 seconds the obtained granules for the compression with magnesium stearate (vegetable magnesium stearate, Taihei Chemical Industry Co., Ltd.) so as to give a weight ratio of 100/0.5 (the granules/magnesium stearate) to formulate a tablet having a diameter of 8.0 mm and a weight of 0.18 g using a rotary tablet press (Clean Press Collect 12HUK (trade name)/manufactured by Kikusui Seisakusho Co., Ltd.). The compression at the time of tableting is adjusted as necessary to give a hardness of 100±10 N after tableting.

Examples of the applicable active pharmaceutical ingredient include orally administerable ingredients such as antipyretic/anti-inflammatory/analgesic drugs, hypnotic/sedative drugs, anti-drowsiness drugs, anti-vertigo drugs, pediatric pain reliever, stomachic drugs, antacid drugs, digestive drugs, cardiotonic drugs, arrhythmic drugs, hypotensive drugs, vasodilator, diuretic drugs, antiulcer drugs, intestinal regulator, therapeutic drugs for osteopolosis, antitussive/expectorant drugs, anti-asthmatic drugs, anti-microbial agents, frequent urination improvement agents, nourishment tonics, and vitamins. The drug effective ingredient may be used singly or in combination of two or more.

The active pharmaceutical ingredients usable in the composition of the present invention are given below, but are not limited thereto.

Examples of the active pharmaceutical ingredient usable in the composition of the present invention include analgesic/anti-inflammatory drugs (NSAIDs, fentanyl, indomethacin, ibuprofen, ketoprofen, nabumetone, paracetamol, piroxicam, tramadol, COX-2 inhibitors such as celecoxib, and rofecoxib), antiarrhythmic agents (procainamide, quinidine, verapamil), antibacterial and antiprotozoal agents (amoxicillin, ampicillin, benzathine penicillin, benzylpenicillin, cefaclor, cefadroxil, cefprozil, cefuroxime axetil, cefalexin, chloramphenicol, chloroquine, ciprofloxacin, clarithromycin, clavulanic acid, clindamycin, doxyxyclin, erythromycin, flucloxacillin sodium, halofantrine, isoniazid, kanamycin sulfate, lincomycin, mefloquine, minocycline, nafcillin sodium, nalidixic acid, neomycin, norfloxacin, ofloxacin, oxacillin, phenoxymethyl-penicillin potassium, pyrimethamine-sulfadoxime, streptomycin), anticoagulant agent (walfarin), antidepressant agents (amitriptyline, amoxapine, butriptyline, clomipramine, desipramine, dothiepin, doxepin, fluoxetine, reboxetine, aminaeptine, selegiline, gepirone, imipramine, lithium carbonate, meanserin, milnacipran, nortriptyline, paroxetine, sertraline; 3-[2-[3,4-dihydrobenzofuran[3,2-c]pyridin-2(1H)-yl]ethyl]-2-methyl-4H-pyrido[1,2-a]pyrimidin-4-one, antidiabetic agents (glibenclamide, metformin), antiepilepsy agents (carbamazepine, clonazepam, ethosuximide, gabapentin, lamotrigine, lavetiracetam, phenobarbitone, phenytoin, primidone, tiagabine, topiramate, valpromide, vigabatrin), antimicrobial agents (amphotericin, clotrimazole, econazole, fluconazole, flucytosine, griseofulvin, itraconazole, ketoconazole, miconazole nitrate, nystatin, terbinafine, voriconazole)), antihistamine agents (astemizole, cinnarizine, cyproheptadine, decarboethoxyloratadine, fexofenadine, flunarizine, levocabastine, loratadine, norastemizole, oxatomide, promethazine, terfenadine, antihypertensive agents (captopril, enalapril, kentaserine, lisinopril, minoxidil, prazosin, ramipril, reserpine, terazosin), antimuscarinic agents (atropine sulfate, hyoscine), antitumor agents and metabolic antagonists (platinum compounds such as cisplatin and carboplatin; taxanes such as paclitaxel, and docetaxel, tecans such as camptothecin, irinotecan, and topotecan; vinca alkaloids such as vinblastine, vindesine, vincristine, and vinorelbine; nucleoside derivatives and folicacid antagonists such as 5-fluorouracil, capecitabine, gemcitabine, mercaptopurine, thioguanine, cladribine, and methotrexate; nitrogen mustard such as cyclophosphamide, chlorambucil, chlormethine, iphosphamide, melphalan, or nitrosourea such as carmustine, lomustine and like alkylating agents, or other alkylating agents such as busulfan, dacarbazine, procarbazine, thiotepa, daunorubicin, doxorubicin, idarubicin, epirubicin, bleomycin, dactinomycin, mitomycin and like antibiotics, HER 2 antibodies such as trastuzumab; podophyllotoxin derivatives such as etoposide, and teniposide, anthraquinone derivatives such as famesyl transferase inhibitor; mitozantrone), antimigraine agents (alniditan, naratriptan, sumatriptan)), antiparkinsonian agents (bromocryptine mesylate, levodopa, selegiline), antipsychotics, hypnotic and sedative agents (alprazolam, buspirone, chlordiazepoxide, chlorpromazine clozapine, diazepam, flupenthixol, fluphenazine, flurazepam, 9-hydroxyrisperidone, lorazepam, mazapertine, olanzapine, oxazepam, pimozide, pipamperone, piracetam, promazine, risperidone, selfotel, seroquel, sertindole, sulpiride, temazepam, thiothixene, triazolam, trifluperidol, ziprasidone, zolpidem), antiseizure agents (lubeluzole, lubeluzole oxide, riluzole, aptiganel, eliprodil, remacemide), antitussive agents (dextromethorphan, laevodropropizine), antivirotic agents (aciclovir, ganciclovir, loviride, tivirapine, zidovudine, lamivudine, zidovudine+lamivudine, didanosine, zalcitabine, stavudine, abacavir, lopinavir, amprenavir, nevirapine, efavirenz, delavirdine, indinavir, nelfinavir, ritonavir, saquinavir, adefovir, hydroxyurea), beta-adrenergic receptor agents (atenolol, carvedilol, metoprolol, nebivolol, propanolol), cardiac inotropic agents (amrinone, digitoxin, digoxin, milrinone), corticosteroids (beclomethasone dipropionate, betamethasone, budesonide, dexamethasone, hydrocotisone, methylprednisolone, prednisolone, prednisone, triamcinolone), germicides (chlorhexidine), diuretic agents (acetazolamide, frusemide, hydrochlorothiazide, isosorbide), enzymes, essential oils (anethole, aniseed oil, caraway, cardamom, cassia oil, cineole, cinnamon oil, clove oil, coriander oil, dementholised mint oil, dill oil, eucalyptus oil, eugenol, ginger, lemon oil, mustard oil, neroli oil, nutmeg oil, orange oil, peppermint, sage, spearmint, terpineol, thyme), digestive drugs (cimetidine, cisapride, clebopride, diphenoxylate, domperidone, famotidine, lansoprazole, loperamide, loperamide oxide, mesalazine, metoclopramide, mosapride, nizatidine, norcisapride, olsalazine, omeprazole, pantoprazole, perprazole, prucalopride, rabeprazole, ranitidine, ridogrel, suphasalazine), hemostats (aminocaproic acid), lipid modifiers (atorvastine, cerivastatin, pravastatin, probucol, simvastatin), local anesthetics (benzocaine, lignocaine), opioid painkillers (buprenorphine, codeine, dextromoramide, dihydrocodeine, hydrocodone, oxycodone, morphine), parasympathetic nerve system and antidementia agents (AIT-082, eptastigmine, galanthamine, metrifonate, milameline, neostigmine, physostigmine, tacrin, donepezil, rivastigmine, sabcomeline, talsaclidine, xanomeline, memantine, lazabemide), peptides and proteins (antibody, becaplermine, ciclosporin, erythropoietin, immunoglobulin, insulin), sex hormones (estrogen: conjugated estrogen, ethinylestradiol, mestranol, estradiol, estriol, estrone; progesterone; chlormadinone acetate, cyproterone acetate, 17-deacetyl norgestimate, desogestrel, dienogest, dydrogesterone, ethynodiol diacetate, gestodene, 3-keto desogestrel, levonorgestrel, lynestrenol, methoxyprogesterone acetate, megesterol, norethindrone, norethindrone acetate, norethisterone, norethisterone acetate, norethynodrel, norgestimate, norgestrel, norgestrienone, progesterone, quingestanol acetate, stimulant (sildenafil), vasodilators (amlodipine, buflomedil), amyl nitrite, diltiazem, dipyridamole, glyceryl trinitrate, isosorbide dinitrate, lidoflazine, molsidomine, nisaldipine, nifedipine, oxpentifylline, pentaerythritol trinitrate), N-oxide of the above substances, pharmaceutically acceptable acid or base addition salts of the above substance and stereochemical isomers of the above substances.

The composition comprising the processed starch powder of the present invention and one or more active ingredients may contain as necessary, in addition to the active ingredients, binder, plasticizer, lubricant, flavoring agent, perfume, colorant, sweetener, etc. These other ingredients may be used as a diluent.

Examples of the binder include saccharides such as refined sugar, glucose lactose, fructose, and trehalose, sugar alcohols such as mannitol, xylitol, maltitol, erythritol, and sorbitol, water soluble polysaccharides such as gelatin, pullulan, carrageenan, locust bean gum, agar, glucomannan, xanthan gum, tamarind gum, pectin, sodium alginate, and gum arabic, celluloses such as microcrystalline celluloses (e.g., "CEOLUS" (registered trade name), manufactured by Asahi Kasei Chemicals Corporation, PH-101, PH-101D, PH-101L, PH-102, PH-301, and PH-301Z, PH-302, PH-F20, PH-M06, M15, M25, KG-801, KG-802, KG-1000, UF-711, UF-702, etc.), powder cellulose, hydroxypropyl cellulose, and methylcellulose, starches such as pregelatinized starch, and starch pastes, synthetic polymers such as polyvinyl pyrrolidone, carboxy vinyl polymer, and polyvinyl alcohol, inorganic compounds such as calcium hydrogenphosphate, calcium carbonate, synthetic hydrotalcite, and magnesium aluminosilicate. One binder selected from the above may be used singly or two or more may be used in combination.

The crystalline cellulose usable as a binder is preferably those having good compression compatibility. By using a crystalline cellulose with good compression compatibility, the tableting can be carried out at a low tableting compression force. Thus, the activity of an active ingredient, which is otherwise inactivated by the compression force, can be maintained, thereby making it possible to form a granule containing tablet and impart the hardness when added in a small amount. Accordingly, a bulky active ingredient can be tableted and a medicament containing many different kinds of active ingredients can be tableted. Further, there are advantages such that a tablet can be downsized in some cases, the tablet has good supporting properties of a liquid ingredient and the compression impediments can be controlled. Examples of the usable commercially available microcrystalline cellulose with good compression compatibility include "CEOLUS" (registered trademark) KG-801, KG-802, KG-1000, UF-711, UF-702 (manufactured by Asahi Kasei Chemicals Corporation).

Examples of the plasticizer include silicon compounds such as a water silicon dioxide and light anhydrous silicic acid. The plasticizer may be used singly or two or more may be used in combination.

Examples of the lubricant include magnesium stearate, calcium stearate, stearic acid, sucrose ester of fatty acids, talc, magnesium alum inometasilicate, water silicon dioxide and light anhydrous silicic acid. One lubricant selected from the above may be used singly or two or more may be used in combination.

Examples of the flavoring agent include glutamic acid, fumaric acid, succinic acid, citric acid, sodium citrate, tartaric acid, malic acid, ascorbic acid, sodium chloride and 1-menthol. One flavoring agent selected from the above may be used singly or two or more may be used in combination.

Examples of the perfume include orange, vanilla, strawberry, yogurt, menthol, fennel oil, cinnamon oil, bitter orange oil, mentha oil, and like oils, and green tea powder. One perfume selected from the above may be used singly or two or more may be used in combination.

Examples of the colorant include food colorants such as Food Red No. 3, Food Yellow No. 5, and Food Blue No. 1, sodium copper chlorofin, titanium oxide, and riboflavin. One colorant selected from the above may be used singly or two or more may be used in combination.

Examples of the sweetener include aspartame, saccharin, dipotassium glycyrrhizate, stevia, maltose, maltitol, starch syrup, amacha powder and the like. One sweetener selected from the above may be used singly or two or more may be used in combination.

Further, a disintegrant may be added insofar as the effects of the present invention are not affected. Examples of the disintegrant include celluloses such as croscarmellose sodium, carmellose, carmellose calcium, carmellose sodium, and low substituted hydroxypropyl cellulose, starches such as carboxymethyl starch sodium, hydroxypropyl starch, rice starch, wheat starch, cornstarch, potato starch, and partly pregelatinized starch, celluloses such as crystalline cellulose, and powdered cellulose, synthetic polymers such as crospovidone, and crospovidone copolymer. One disintegrant selected from the above may be used singly or two or more may be used in combination. However, an attention must be paid not to impair the effects of the present invention which provides a disintegrant having good storage stability owing to a low reactivity to an active ingredient and little hygroscopicity as well as having been eaten commonly and being highly safe.

The solid preparation containing the composition comprising the processed starch powder of the present invention and one or more active ingredients can be produced by a method for producing a solid preparation routinely carried out in the field of pharmaceutical products. For example, the direct powder compression method can be employed in which an active ingredient, the processed starch powder and, as necessary, a binder, a disintegrant, a plasticizer, a flavoring agent, a perfume, a colorant, a sweetener, etc., are uniformly mixed and subsequently compressed. Other examples include wet granulation compression method and dry granulation compression method in which an active ingredient, the processed starch powder and, as necessary, a binder, a disintegrant, a plasticizer, a flavoring agent, a perfume, a colorant, a sweetener, etc., are wet granulated (extrusion granulation, fluidized bed granulation, tumbling fluidized bed granulation, etc.), or dry granulated (crushing granulation using a roller compactor, or the like), and ingredients such as a binder, a disintegrant, a plasticizer, a flavoring agent, a perfume, a colorant, a sweetener, etc., are added as necessary to the obtained granule.

The compression compactor for producing solid preparations is not limited and examples include compressors such as static pressure press, single punch tablet press, rotary tablet press, multilayered tablet compactors, and core tablet press.

Further, coating may be applied to a solid preparation itself for the purposes of controlling the elution of an active ingredient, masking flavor, or moisture proofing and the like, unless the effects of the present invention are affected. The usable coating agent(s) is(are) one or more selected from, for example, cellulose coating agents (ethyl cellulose, hydroxypropyl methylcellulose phthalate, carboxy methyl ethyl cellulose, hydroxypropyl methylcellulose acetate succinate, cellulose acetate succinate, cellulose acetate phthalate, cellulose acetate, etc.), acrylic polymer coating agents (Eudragit RS, Eudragit L, Eudragit NE, etc.), shellac, and silicone resins. The method for using these coating agents can be those which have been known in the art. The coating agent may be dissolved in an organic solvent or suspended in water for use.

EXAMPLES

The present invention is described below in detail with reference to examples, but is not limited thereto. Each test method and property measurement method in Examples and Comparative Examples are as follows.

(1) Swelling Ratio of Primary Particles in Dry State to Primary Particles in Swollen State in Water.

An optical microscope image of the processed starch powder is processed by an image analysis treatment (manufactured by InterQuest, Co., Ltd., processor: Hyper 700, software: Imagehyper), and the long side of a rectangle having the smallest area among the rectangles circumscribing particles was determined as the primary particle size of the particle. The average particle size $W1$ (μm) of the primary particles in the dry state was an average value of at least 400 particles. The optical microscope images are taken in the manner that a small amount of samples is scattered on the stage so that individual particles do not overlap, and those obviously overlapped and not distinguishable as the primary particles are excluded at the time of the image analysis while the measurement. Subsequently, 200 g of pure water in a temperature range of 20° C.±5° C. was put in a container, 1.0 g of the processed starch was added thereto over the period of 2 minutes while stirring using a magnetic stirrer at 500 rpm, and was dispersed for 3 minutes after the addition. The obtained dispersion was ultrasonically treated (SHARP CORPORATION, SILENTSONIC (trade name), UC-6200, high frequency output 600 W, 40 kHz) for 5 minutes and a part of the dispersion was observed using an optical microscope. The observation was carried out under a magnification such that 20 particles or more are present within the sight, and the maximum sizes of all distinguishable primary particles were measured. The measurement of the maximum size were repeated five times, and the average value of the maximum sizes of all particles based on the five-times measurement was determined to be the average particle size $W2$ (μm) of the primary particles in the swollen state. The maximum size of the primary particles used herein refers to the maximum length of the straight line connecting one end to the other of the primary particle. Further, the primary particle herein refers to the particle having the same constituting unit as the raw starch grain, but those not clearly identified as the primary particle due to overlapping and aggregation were excluded while the measurement was carried out.

The swelling ratio of the primary particles in the dry state to the primary particles in the swollen state in water was defined as the value determined by these values and the following formula (1).

$$\text{Swelling ratio of primary particles in dry state to primary particles in swollen state in water} = W2 \ (\mu m)/W1 \ (\mu m) \quad (1)$$

(2) Water Soluble Component amount (% by Weight)

97 g of pure water in the range of 20° C.±5° C. was added to 3 g of the processed starch, dispersed by stirring for 2 hours using a magnetic stirrer, and 40 cm³ of the obtained dispersion moved to a 50 cm³ centrifuge tube was centrifuged at 5000 G for 15 minutes. 30 cm³ of the supernatant was put in a weighing bottle and dried at 110° C. to a certain weight whereby a dry weight (g) of the water soluble component was determined. Further, an absolute dry weight (g) of the processed starch was determined by drying 1 g of the processed starch at 110° C. to a certain weight. The amount of the water soluble component was defined as the value determined by these values and the formula (2) below.

$$\text{Water soluble component amount (\% by weight)} = (\text{dry weight (g)} \times 100 \div 30) \div \text{absolute weight (g) of 1 g of processed starch} \times 100 \quad (2)$$

(3) Water Retention Capacity (%)

Processed starch W0 (g) (about 1 g) was gradually put to a 50 cm³ centrifugation tube in which about 15 cm³ of pure water in a temperature range of 20° C.±5° C. was placed and dispersed in the pure water until the mixture became clear to translucence while stirring for about 2 minutes using a spatula. The pure water in a temperature range of 20° C.±5° C. was further added so that the mixture filled up about 70% of a 50 cm³ sedimentation tube and the centrifugation (2000 G, 10 minutes) was carried out. Within 1 minute after the completion of the centrifugation, the separated upper layer was cut off and a water retention capacity was determined based on the weight W (g) remained in the lower layer (starch+pure water amount retained in the starch) using the following formula (3).

$$\text{Water retention capacity (\%)} = 100 \times (W - W0)/W0 \quad (3)$$

(4) Sedimentation Volume (cm³/g)

70 g of pure water in the range of 20±5° C. was put in a container, 1.0 g of the processed starch was added thereto over the period of about 2 minutes while stirring using a magnetic stirrer at 500 rpm, and was dispersed for 3 minutes after the addition. The dispersion was moved to a 100 cm³ sedimentation tube and the dispersion adhered to the container was washed using pure water to give a total amount of 100 cm³ which was allowed to stand for 16 hours. Then, the volume V (cm³) of the bottom layer among the separated top and bottom layers and the absolute weight (g) of 1.0 g of the processed starch were measured, whereby the sedimentation volume (cm³/g) was determined by the following formula (4) (the absolute weight herein was determined in the same manner as in the calculation of the water soluble component amount).

$$\text{Sedimentation volume (cm}^3\text{/g)} = V \ (\text{cm}^3)/\text{absolute weight (g) of 1.0 g of processed starch}$$

(5) Average Particle Size of Primary Particles in Swollen State in Water

The value of the W2 (μm) measured in the above (1) was used.

(6) Average Particle Size of Primary Particles in Dry State

The value of the W1 (μm) measured in the above (1) was used.

(7) Outer Shell Structure 200 g of pure water in the range of 20° C.±5° C. was put in a container, 1.0 g of the processed starch was added thereto over the period of 2 minutes while stirring using a magnetic stirrer at 500 rpm, and was dispersed for 3 minutes after the addition. The obtained dispersion was ultrasonically treated for 5 minutes and a part of the dispersion was observed using an optical microscope. The processed particle powder of the present invention had the outer shell structure derived from a raw starch material. Having the outer shell structure herein means that 90% or more of the total particles numbers maintain the outer shell structure inherently found in a starch material when observed using an optical microscope in the magnification such that 20 or more particles were present within the sight. The particles which were unclear as being a single primary particle or not due to the aggregation or overlapping of a plurality of particles were excluded before the measurement was carried out.

(8) Nonbirefringent Particles 200 g of pure water in the range of 20° C.±5° C. was put in a container, 1.0 g of the processed starch was added thereto over the period of 2 minutes while stirring using a magnetic stirrer at 500 rpm, and was dispersed for 3 minutes after the addition. The obtained dispersion was ultrasonically treated for 5 minutes and a part of the dispersion was observed using an optical microscope. A birefringent particle shows a so-called polarized cross pattern which has a luminance at the four corners thereof, but the birefringent particle in the present invention is defined as that having two or more distinct luminances out of four particle corners. The particles in which one luminance was clear but the other was unclear were excluded. Based on the total number of the primary particles and the number of the birefringent particles as defined in the present invention, the numbers of nonbirefringent particles (=total particles–the number of birefringent particles as defined in the present invention) were determined and divided by the total particle number to determine the proportion (percentage) of the nonbirefringent particles. The processed starch of the present invention has a proportion of the nonbirefringent particles of 90% or more to the total number of the distinguished primary particles. The nonbirefringent particle herein means that the proportion of the non-birefringent particles is 90% or more to the total number of the distinguished primary particles. The distinguished primary particles refer to those distinctively distinguishable as an individual primary particle and exclude those in the condition of being unclear as an individual primary particle. When there are many particles in such an unclear condition, an adjustment is made as necessary by extending the ultrasonic treatment time described above or diluting with pure water.

(9) Disintegration Time (Second)

The disintegration time (second) is defined as a disintegration time in a test solution of a cylindrical compact having a diameter of 1.13 cm obtained by compacting 0.5 g of a formulated powder using a static pressure press (MODEL-1321DW CREEP/manufactured by Aiko Engineering Co., Ltd.) at a compressive force of 130 MPa. The test solution was the second solution (pH 6.8) described in the 14th edition of Japanese pharmacopeia, and the disintegration test was conducted in accordance with the disintegration test method of the 15th edition of Japanese pharmacopeia without using an auxiliary disc.

(10) Tablet Hardness

The tablet hardness was measured using a SCHLEUNIGER hardness tester (Model 8D, FREUND, import and sales).

(11) Disintegration Test

The disintegration test was conducted in accordance with the disintegration test method described in the 15th edition of Japanese pharmacopeia using a disintegration tester (NT-40 HS, Toyama Sangyo Co., Ltd.) under the conditions of pure water at 37° C. without using a disc.

Example 1

Potato starch was put in a stainless pan (50 cm×25 cm) to a layer thickness of 5 cm, left for 5 minutes at a reduced pressure (600 mmHg) in a pressure resistant container and moist-heat treated for 20 minutes with pressurized steam (120° C.). The moist-heat treated potato starch was dispersed in pure water to prepare a starch slurry having a solid content of 10% by weight. The starch slurry was heated and gelatinized (outlet temperature 72° C.) using a jet cooker at 20 L/hr and subsequently spray dried, thereby obtaining a processed starch A. The basic physical properties of the obtained processed starch A were shown in Table 1, and optical microscope images of the particle shape in the swollen state in water were shown in FIGS. 5(a) and (b) ((b) is a polarized photograph). The particle shape in the swollen state in water was observed using a microscope (digital microscope KH-1300 (trade name), manufactured by HIROX Co., Ltd.) under the conditions of a magnification of x350 and transmitted light. Further, the particle shape under polarized light was observed by adjusting the levels of light quantity and the polarization so that unpolarized particles were not observed and only polarized area was penetrated by light and observed.

Figure 5A:
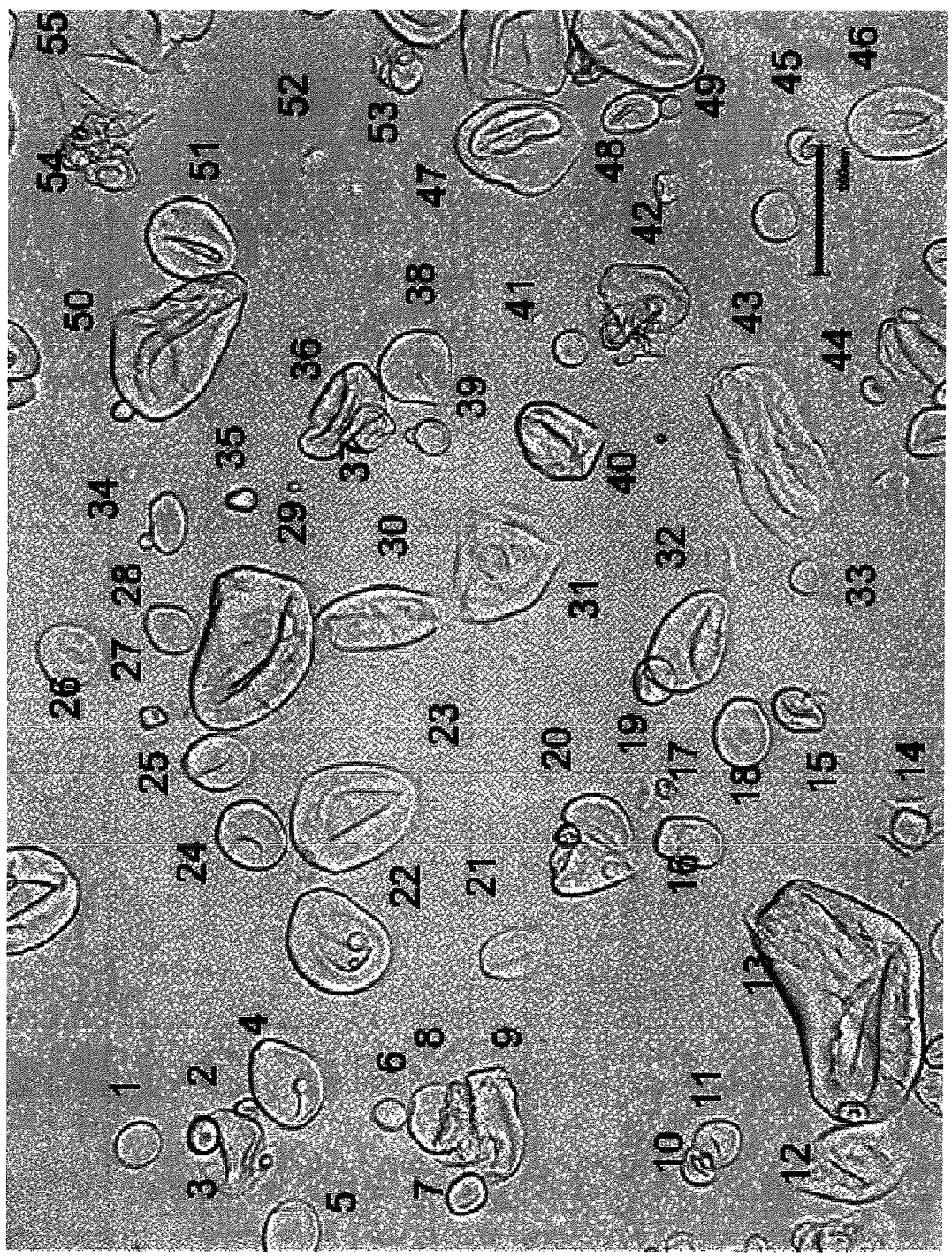
FIG. 5a is a drawing showing an optical microscope photograph of the particle morphology of processed starch A swollen in water (Example 1) (not polarized)
Figure 5B:
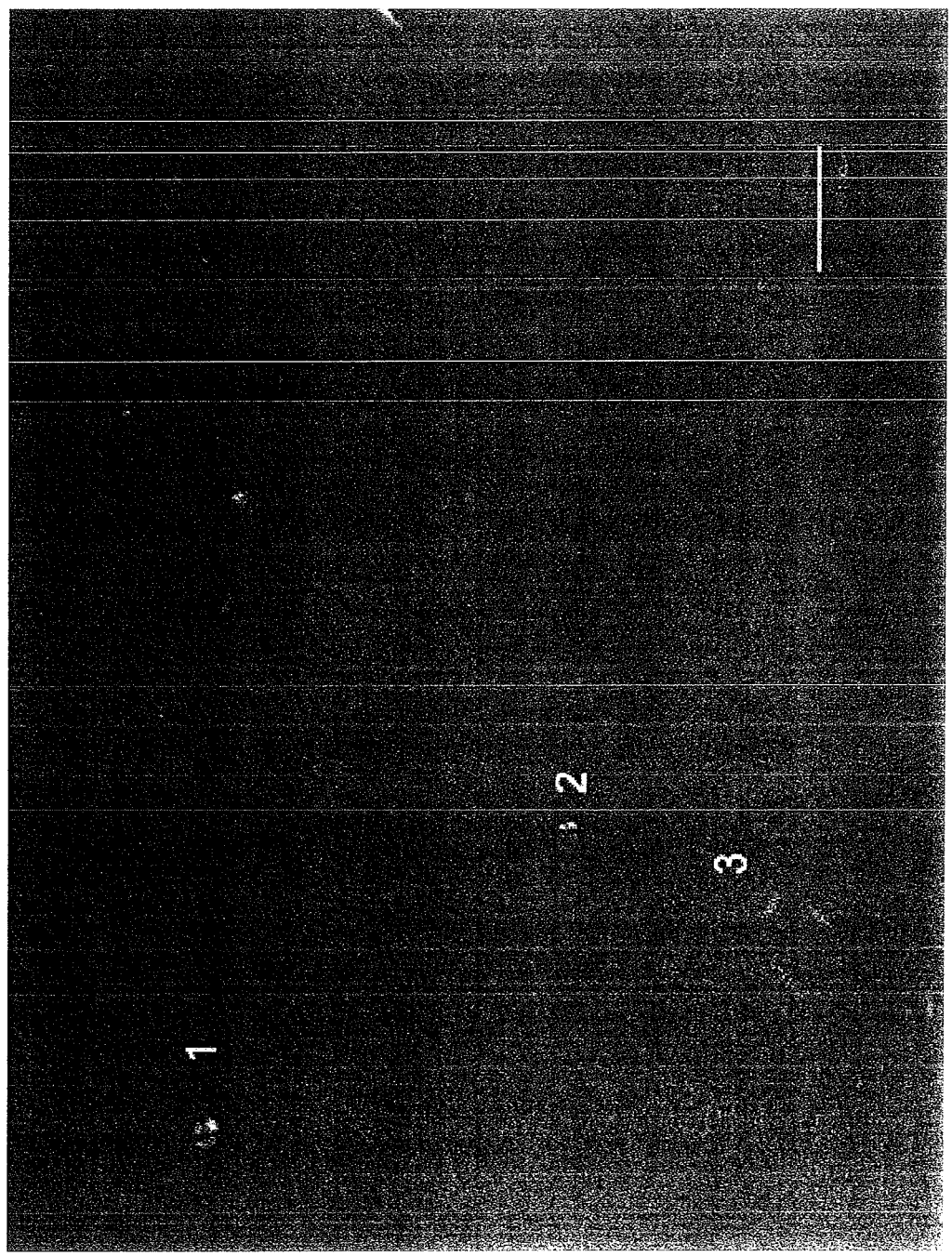
FIG. 5b is a drawing showing an optical microscope photograph of the particle morphology of processed starch A swollen in water (Example 1) (polarized)
Figure 12A:
FIG. 12a is a drawing showing an optical microscope photograph of the particle morphology of a natural cornstarch swollen in water (not polarized)
Figure 12B:
FIG. 12b is a drawing showing an optical microscope photograph of the particle morphology of a natural cornstarch swollen in water (polarized)
Figure 13A:
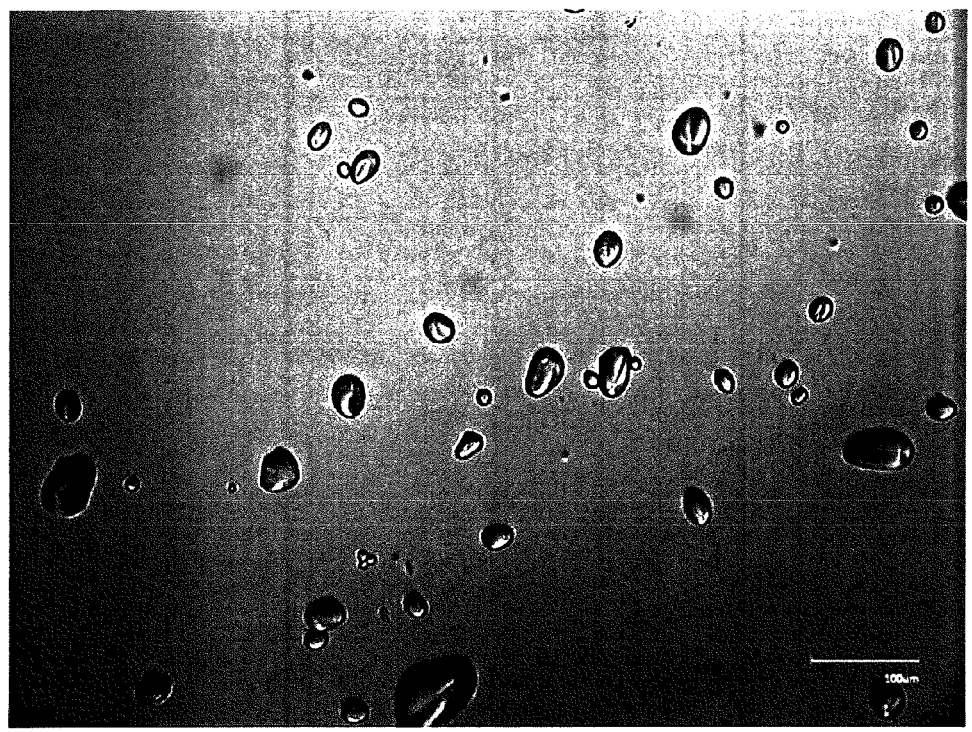
FIG. 13a is a drawing showing an optical microscope photograph of the particle morphology of natural potato starch swollen in water (not polarized)
Figure 13B:
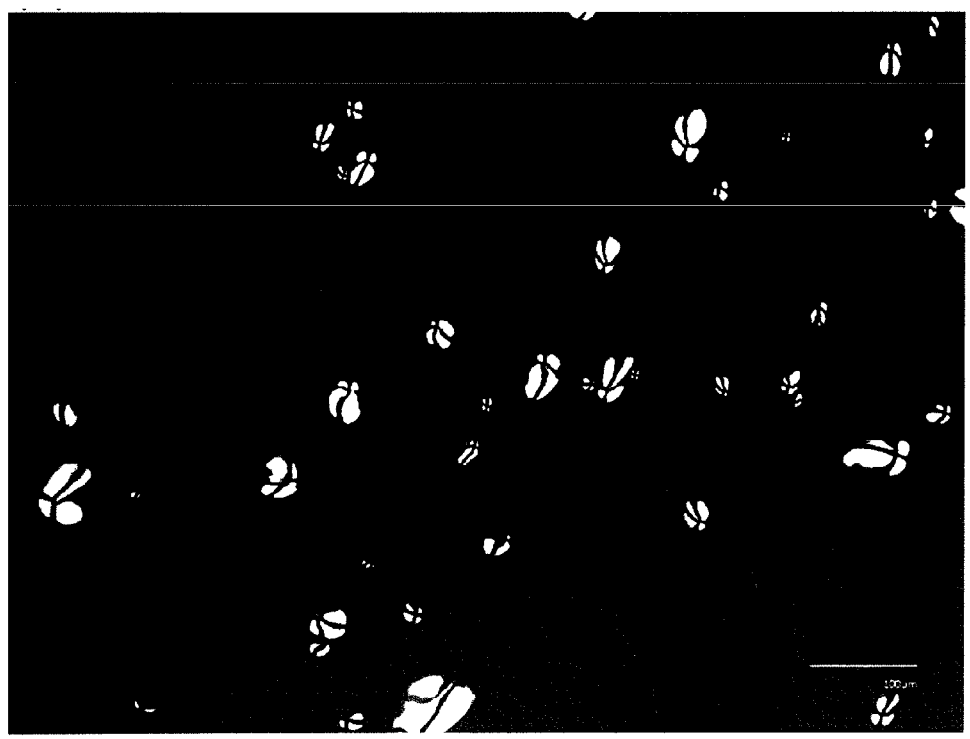
FIG. 13b is a drawing showing an optical microscope photograph of the particle morphology of natural potato starch swollen in water (polarized).

The processed starch A exhibited desirable values in the water retention capacity, amount of the water soluble components, sedimentation volume, particle size in the dry state and particle size in the swollen state (see Table 1), was free of the breakage of outer shell structure, composed of the primary particle which is the same constituent unit as a natural starch grain and had a preferable value in the swelling ratio of the primary particles in the dry state to the primary particles in the swollen state in water (see FIG. 5(a)). The proportion of the nonbirefringent particles in the swollen state in water was 94.5%. (See FIG. 5(b)). It was evidently different from the birefringent natural starch (FIG. 12 showing cornstarch and FIG. 13 showing potato starch) which shows a distinct polarized cross.

Using the obtained processed starch A as a disintegrant, tablets containing ethenzamide as active ingredient were prepared by the following three methods.

Direct Compression Method

The processed starch A, ethenzamide (API Corporation), a microcrystalline cellulose ("CEOLUS" (registered trade name) KG-802, manufactured by Asahi Kasei Chemicals Corporation), lactose granule (Super-Tab (trade name), Asahi Kasei Chemicals Corporation) and a light anhydrous silicic acid (Aerosil 200 (trade name), Nippon Aerosil Co., Ltd.) were uniformly mixed so as to give a weight ratio of 3/30/10/57/1. Subsequently magnesium stearate (vegetable magnesium stearate, Taihei Chemical Industry Co., Ltd.) was added to the mixed particles so as to give a weight ratio of 100/0.5 (the mixed particles/magnesium stearate), and slowly mixed to formulate a tablet having a diameter of 8.0 mm and a weight of 0.18 g using a rotary tablet press (Clean Press Collect 12HUK (trade name)/manufactured by Kikusui Seisakusho Co., Ltd.) at force of 5 or 8 kN.

High Shear Granulation/Compression Method

The processed starch A, ethenzamide (API Corporation), a microcrystalline cellulose ("CEOLUS" (registered trade name) PH-101, manufactured by Asahi Kasei Chemicals Corporation) and lactose granule (200 mesh lactose, manufactured by DMV) were uniformly mixed so as to give a weight ratio of 3/30/10/57 and the mixture was wet-granulated in a stirring granulator (VG-10, manufactured by Powrex Corp.) using an 8% HPC-L (manufactured by NIPPON SODA CO., LTD.) as a binder under the conditions of a blade rotation number of 210 rpm, a cross chopper rotation number of 2000 rpm. The obtained granules were dried at 60° C. for 16 hours, and subsequently coarse particles were removed using a sieve having an opening of 1400 μm to obtain granules for the compression. The obtained granules for the compression were slowly mixed with magnesium stearate (vegetable magnesium stearate, Taihei Chemical Industry Co., Ltd.) so as to give a weight ratio of 100/0.5 (the granules/magnesium stearate) to formulate a tablet having a diameter of 8.0 mm and a weight of 0.18 g using a rotary tablet press (Clean Press Collect 12HUK (trade name)/manufactured by Kikusui Seisakusho Co., Ltd.) at force of 8 or 10 kN.

Fluidized Bed Granulation/Compression Method

The processed starch A, ethenzamide (API Corporation), a microcrystalline cellulose ("CEOLUS" (registered trade name) PH-101, manufactured by Asahi Kasei Chemicals Corporation) and crystallized lactose (200 mesh lactose, manufactured by DMV International) were uniformly mixed so as to give a weight ratio of 1/30/10/59, the mixture was wet-granulated in a fluidized bed granulator (MP-01, manufactured by Powrex Corp.) using a 6% HPC-L (manufactured by NIPPON SODA CO., LTD.) as a binder under the condition of drying the mixture until an exhaust-air temperature reaches 40° C. in the spray conditions of, at the fluidized bed top spray and bottom spray, 0.1 MPa, 30 L/min, air flow rate 20 to 40 m³/hr, charge-air temperature 75° C., exhaust-air temperature in due course (28 to 33° C.) and spray solution rate: about 7 g/min. The coarse particles were removed using a sieve having an opening of 700 μm from the obtained granules to obtain granules for the compression. The obtained granules for the compression was slowly mixed with magnesium stearate (vegetable magnesium stearate, Taihei Chemical Industry Co., Ltd.) so as to give a weight ratio of 100/0.5 (the granules/magnesium stearate) to formulate a tablet having a diameter of 8.0 mm and a weight of 0.18 g using a rotary tablet press (Clean Press Collect 12HUK (trade name)/manufactured by Kikusui Seisakusho Co., Ltd.) at force of 5 or 7 kN.

The disintegration tests for the tablets obtained by direct compression, high shear granulation/compression and fluidized bed granulation/compression, respectively, were carried out and the test results were shown in Table 2 together with the results of the tests conducted in the same manner in Examples 2 to 5 and Comparative Examples 1 to 13 to be described later. All of the tablets in any of the tablet compression methods in which the processed starch A having the swelling ratio of the primary particles in the dry state to the primary particles in the swollen state in water, water soluble component amount and water retention capacity within the ranges of the present invention was used as a disintegrant had fast disintegration time which was the same level as those of croscarmellose sodium and crospovidone.

Example 2

The processed starch B was manufactured in the same manner as in Example 1 except that an outlet temperature for heating and gelatinizaiton was 76° C. The basic physical properties of the processed starch B were shown in Table 1. Subsequently, tablets were prepared by three methods, direct compression, high shear granulation/compression and fluidized bed granulation/compression, in the same manner as in Example 1 except that the processed starch B was used in place of the processed starch A, and the results of the disintegration test conducted were shown in Table 2. All of the tablets in any of the tablet compression methods in which the processed starch B having the swelling ratio of the primary particles in the dry state to the primary particles in the swollen state in water, water soluble component amount, water retention capacity and sedimentation volume within the ranges of the present invention was used as a disintegrant had fast disintegration time which was the same level as those of croscarmellose sodium and crospovidone.

Example 3

The processed starch C was manufactured in the same manner as in Example 1 except that an outlet temperature for heating and gelatinizaiton was 80° C. The basic physical properties of the processed starch C were shown in Table 1. Subsequently, tablets were prepared by three methods, direct compression, high shear granulation/compression and fluidized bed granulation/compression, in the same manner as in Example 1 except that the processed starch C was used in place of the processed starch A, and the results of the disintegration test conducted were shown in Table 2. All of the tablets in any of the tablet compression methods in which the processed starch C having the swelling ratio of the primary particles in the dry state to the primary particles in the swollen state in water, water soluble component amount, water retention capacity and sedimentation volume within the ranges of the present invention was used as a disintegrant had fast disintegration time which was the same level as those of croscarmellose sodium and crospovidone.

Example 4

The processed starch D was manufactured in the same manner as in Example 1 except that an outlet temperature for heating and gelatinizaiton was 84° C. The basic physical properties of the processed starch D were shown in Table 1. Subsequently, tablets were prepared by three methods, direct compression, high shear granulation/compression and fluidized bed granulation/compression, in the same manner as in Example 1 except that the processed starch D was used in place of the processed starch A, and the results of the disintegration test conducted were shown in Table 2. All of the tablets in any of the tablet compression methods in which the processed starch D having the swelling ratio of the primary particles in the dry state to the primary particles in the swollen state in water, water soluble component amount, water retention capacity and sedimentation volume within the ranges of the present invention was used as a disintegrant had fast disintegration time which was the same level as those of croscarmellose sodium and crospovidone.

Example 5

The processed starch E was manufactured in the same manner as in Example 1 except that an outlet temperature for heating and gelatinizaiton was 88° C. The basic physical properties of the processed starch E were shown in Table 1. Subsequently, tablets were prepared by three methods, direct compression, high shear granulation/compression and fluidized bed granulation/compression, in the same manner as in Example 1 except that the processed starch E was used in place of the processed starch A, and the results of the disintegration test conducted were shown in Table 2. All of the tablets in any of the tablet compression methods in which the processed starch E having the swelling ratio of the primary particles in the dry state to the primary particles in the swollen state in water, water soluble component amount, water retention capacity and sedimentation volume within the ranges of the present invention was used as a disintegrant had fast disintegration time which was the same level as those of croscarmellose sodium and crospovidone.

Comparative Example 1

1 kg of potato starch was dispersed in 7 kg of warm water at 60° C., the temperature was increased at a rate of 1° C./min while stirring the slurry and the slurry was heated to 62° C. and 2 kg of water of about 20° C. was added thereto to halt the heat treatment. Subsequently, spray drying was carried out to obtain the processed starch F (corresponding to Example 15 of PATENT DOCUMENT 7). The basic physical properties of the processed starch F were shown in Table 1. Subsequently, tablets were prepared by three methods, direct compression, high shear granulation/compression and fluidized bed granulation/compression, in the same manner as in Example 1 except that the processed starch F was used in place of the processed starch A, and the results of the disintegration test conducted were shown in Table 2.

The obtained tablets in any of the tablet compression methods in which the processed starch F having the smaller swelling ratio of the primary particles in the dry state to the primary particles in the swollen state in water and smaller water retention capacity smaller than the ranges of the present invention was used had only slower disintegration time than that of the processed starches A to E.

Comparative Example 2

The processed starch G was manufactured in the same manner as in Example 1 except that an outlet temperature for heating and gelatinizaiton was 68° C. The basic physical properties of the obtained processed starch G were shown in Table 1, and optical microscope images of the particle shape in the swollen state in water were shown in FIGS. 6(a) and (b) ((b) is a polarized photograph).

Subsequently, tablets were prepared by three methods, direct compression, high shear granulation/compression and fluidized bed granulation/compression, in the same manner as in Example 1 except that the processed starch G was used in place of the processed starch A, and the results of the disintegration test conducted were shown in Table 2.

Figure 6A:
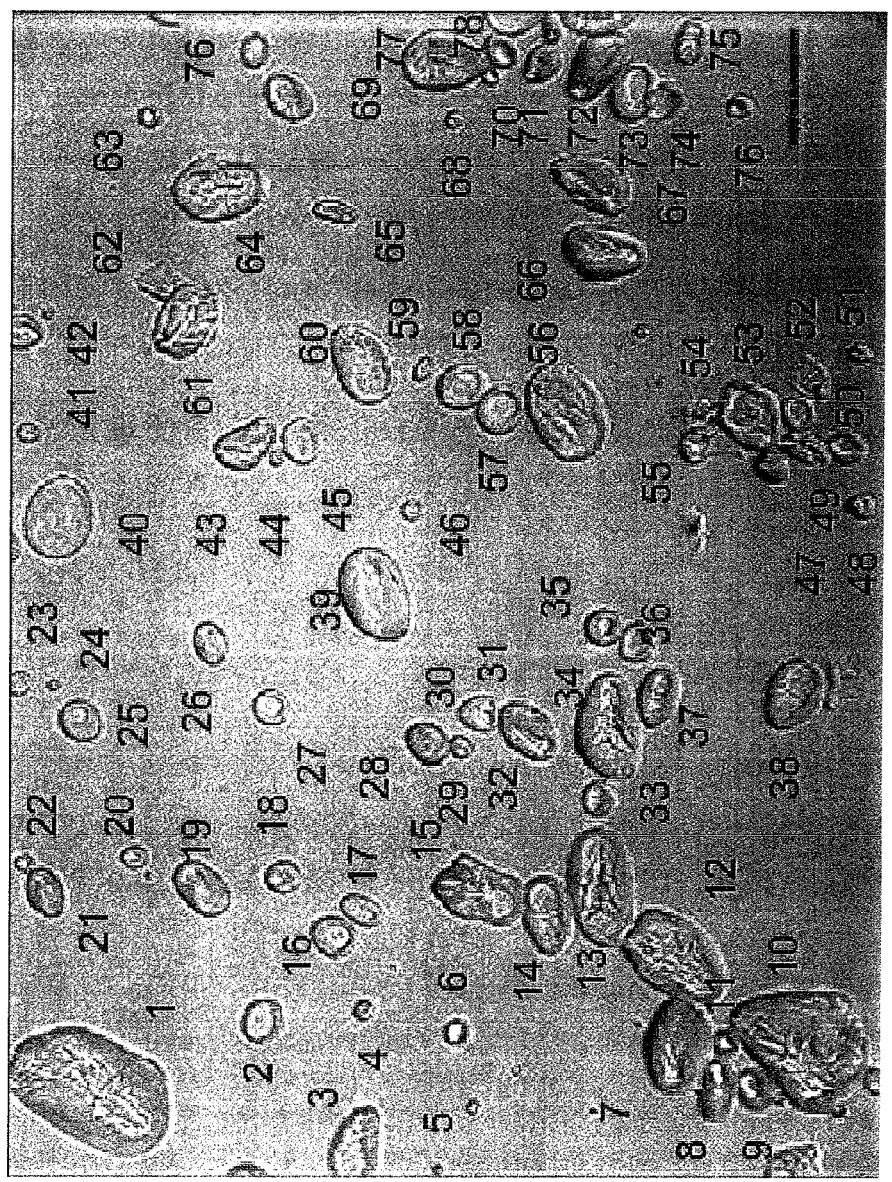
FIG. 6a is a drawing showing an optical microscope photograph of the particle morphology of processed starch G swollen in water (Comparative Example 2) (not polarized)
Figure 6B:
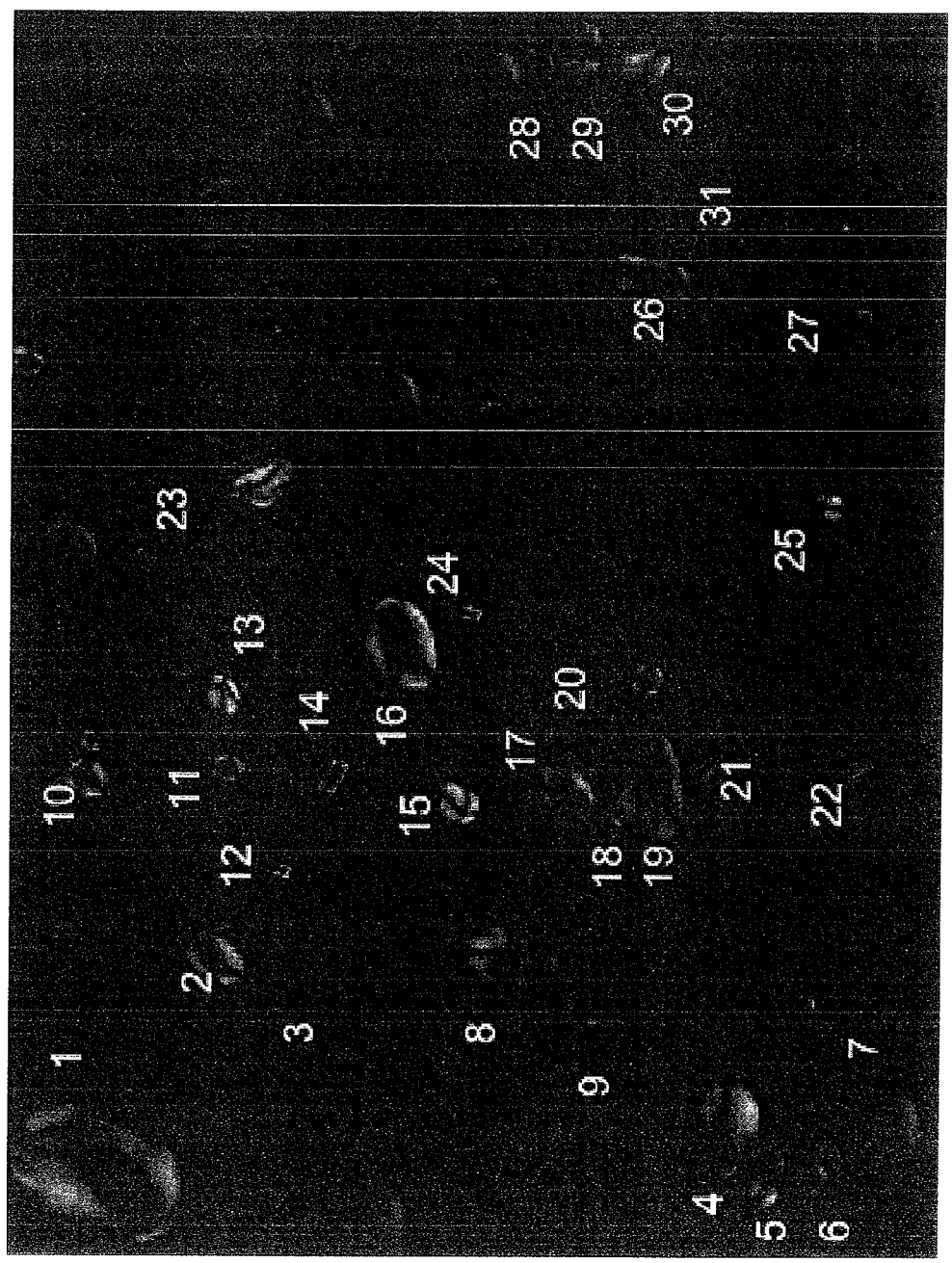
FIG. 6b is a drawing showing an optical microscope photograph of the particle morphology of processed starch G swollen in water (Comparative Example 2) (polarized)

The processed starch G was free of the breakage of outer shell structure (see FIG. 6(a)) but had a smaller swelling ratio of the primary particles in the dry state to the primary particles in a swollen state in water than the range of the present invention (see Table 1). Further, in the swollen state in water, the non-swelling starch particles showing distinct polarized cross as in natural starch were mixed in (See FIG. 6(b)). The obtained tablets in which the processed starch G was used had a comparatively fast disintegration time in the high shear granulation/compression method but had only slow disintegration time in the direct compression method and the fluidized bed granulation/compression method.

Comparative Example 3

The processed starch H was manufactured in the same manner as in Example 1 except an outlet temperature for heating and gelatinizaiton was 92° C. The basic physical properties of the processed starch H were shown in Table 1, and optical microscope images of the particle shape in the swollen state in water were shown in FIGS. 7(a) and (b) ((b) is a polarized photograph).

Subsequently, tablets were prepared by three methods, direct compression, high shear granulation/compression and fluidized bed granulation/compression, in the same manner as in Example 1 except that the processed starch H was used in place of the processed starch A, and the results of the disintegration test conducted were shown in Table 2.

Figure 7A:
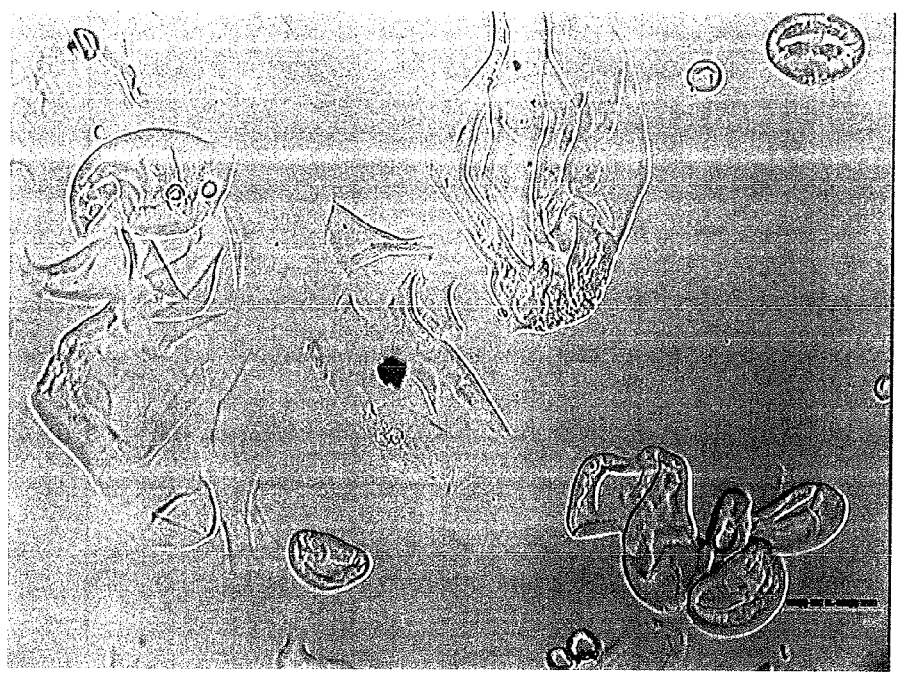
FIG. 7a is a drawing showing an optical microscope photograph of the particle morphology of processed starch H swollen in water (Comparative Example 3) (not polarized)
Figure 7B:
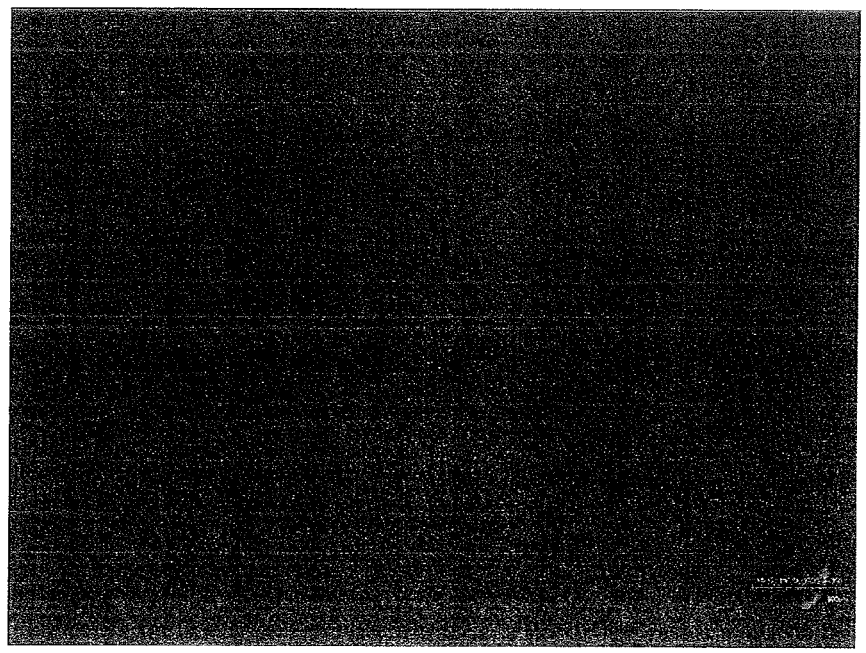
FIG. 7b is a drawing showing an optical microscope photograph of the particle morphology of processed starch H swollen in water (Comparative Example 3) (polarized)

The processed starch H had a higher range of the water soluble component amount than the range of the present invention (see Table 1), and had particles with the broken outer shell structure present with less than 90% of the particles preserving the shape of the primary particle which is the same constituent unit as the natural starch grain (see FIG. 7(a)). The tablet in which the processed starch H was used had a comparatively fast disintegration time in the direct compression method but had only slow disintegration time in high shear granulation/compression method and the fluidized bed granulation/compression.

Comparative Example 4

The processed starch K was manufactured in the same manner as in Example 1 except that an outlet temperature for heating and gelatinizaiton was 90° C. and the basic physical properties thereof were shown in Table 1. Subsequently, tablets were prepared by three methods, direct compression, high shear granulation/compression and fluidized bed granulation/compression, in the same manner as in Example 1 except that the processed starch K was used in place of the processed starch A, and the results of the disintegration test conducted were shown in Table 2.

The processed starch K had the water retention capacity, sedimentation volume, swelling ratio of the primary particles in the dry state to the primary particles in the swollen state in water within the range of the present invention, but the water soluble component amount had a higher range than that of the present invention. The obtained tablets in any of the tablet compression methods in which such a partly pregelatinized starch was used only had slower disintegration time compared with the processed starches A to E.

Comparative Example 5

Figure 8B:
FIG. 8b is a drawing showing an optical microscope photograph of the particle morphology of processed starch I swollen in water (Comparative Example 5) (polarized)

A starch slurry having a solid content of 7.5% by weight was prepared using potato starch which was put in a stainless pan (50 cm×25 cm) in a layer thickness of 5 cm, left for 5 minutes at a reduced pressure (600 mmHg) in a pressure resistant container and moist-heat treated for 20 minutes with pressurized steam (120° C.). The starch slurry was heated and gelatinized (outlet temperature 100° C.) using a jet cooker at 20 L/hr, continuously passed through a retention tube (100° C.) of a 3 L container, followed by spray drying to obtain processed starch I. The basic physical properties of the processed starch I were shown in Actual Table 1 and the optical microscope images of the particle shape in the swollen state in water were shown in FIGS. 8(a) and (b) ((b) is a polarized photograph). This processed starch corresponds to Example 6 of PATENT DOCUMENT 16 and Example 1 of PATENT DOCUMENTS 18 and 19.

Tablets were prepared by three methods, direct compression, high shear granulation/compression and fluidized bed granulation/compression, in the same manner as in Example 1 except that the processed starch I was used in place of the processed starch A, and the results of the disintegration test conducted were shown in Table 2.

The processed starch I had the water soluble component amount greatly beyond the range of the present invention (see Table 1) and many particles had the broken outer shell structure (see (a)). The obtained tablets in any of the tablet compression methods in which the processed starch I was used only had slower disintegration time compared with the processed starches A to E.

Comparative Example 6

Cornstarch was put in a stainless pan (50 cm×25 cm) in a layer thickness of 5 cm, left for 5 minutes at a reduced pressure (600 mmHg) in a pressure resistant container and moist-heat treated for 20 minutes with pressurized steam (115° C.). The moist-heat treated cornstarch was dispersed in pure water to prepare a starch slurry having a solid content of 10% by weight. The starch slurry was heated and gelatinized (outlet temperature 80° C.) using a jet cooker at 20 L/hr and subsequently spray dried, thereby obtaining a processed starch L. The basic physical properties of the obtained processed starch L were shown in Table 1.

Tablets were prepared by three methods, direct compression, high shear granulation/compression and fluidized bed granulation/compression, in the same manner as in Example 1 except that the processed starch L was used in place of the processed starch A, and the results of the disintegration test conducted were shown in Table 2.

The processed starch L had the water soluble component amount, swelling ratio of the primary particles in the dry state to the primary particles in swollen state in water and sedimentation volume within the range of the present invention, but the average particle size of the primary particles in the dry state and in water and the water retention capacity were smaller than the range of the present invention. The obtained tablets in any of the tablet compression methods in which such a partly pregelatinized starch was used only had slower disintegration time compared with the processed starches A to E.

Comparative Example 7

1 kg of potato starch was dispersed in 7 kg of warm water at 60° C., the temperature was increased at a rate of 1° C./min while stirring the slurry and the slurry was heated to 68° C. and 2 kg of water of about 20° C. was added thereto to halt the heat treatment. Subsequently, spray drying was carried out to obtain the processed starch J (corresponding to the lower heating temperature than that of Example 17, sample 7 of PATENT DOCUMENT 6). The basic physical properties of the obtained processed starch J were shown in Table 1, and optical microscope images of the particle shape in the swollen state in water were shown in FIGS. 9(a) and (b) ((b) is a polarized photograph).

Tablets were prepared by three methods, direct compression, high shear granulation/compression and fluidized bed granulation/compression, in the same manner as in Example 1 except that the processed starch J was used, and the results of the disintegration test conducted were shown in Table 2.

Figure 9A:
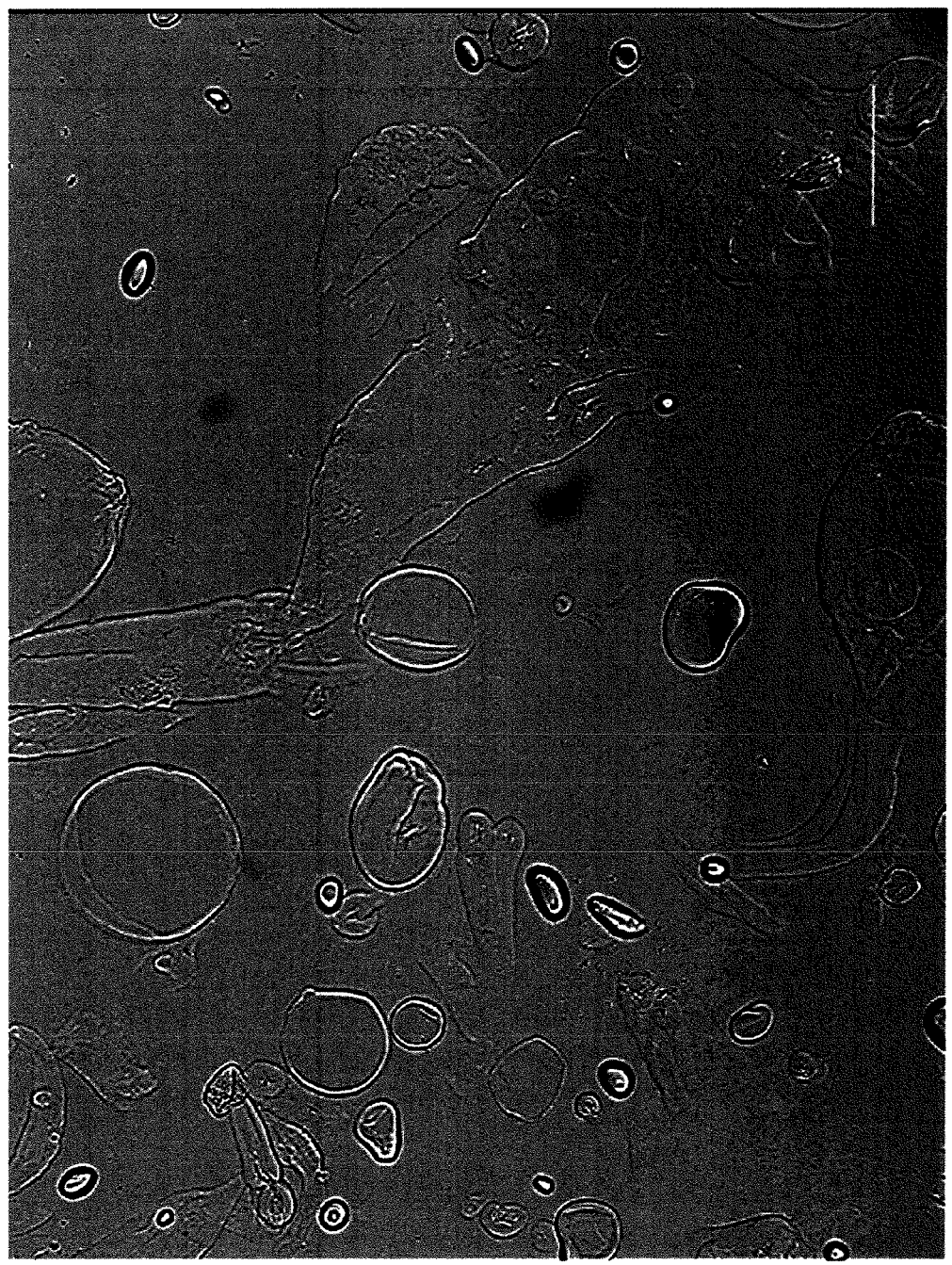
FIG. 9a is a drawing showing an optical microscope photograph of the particle morphology of processed starch J swollen in water (Comparative Example 7) (not polarized)
Figure 9B:
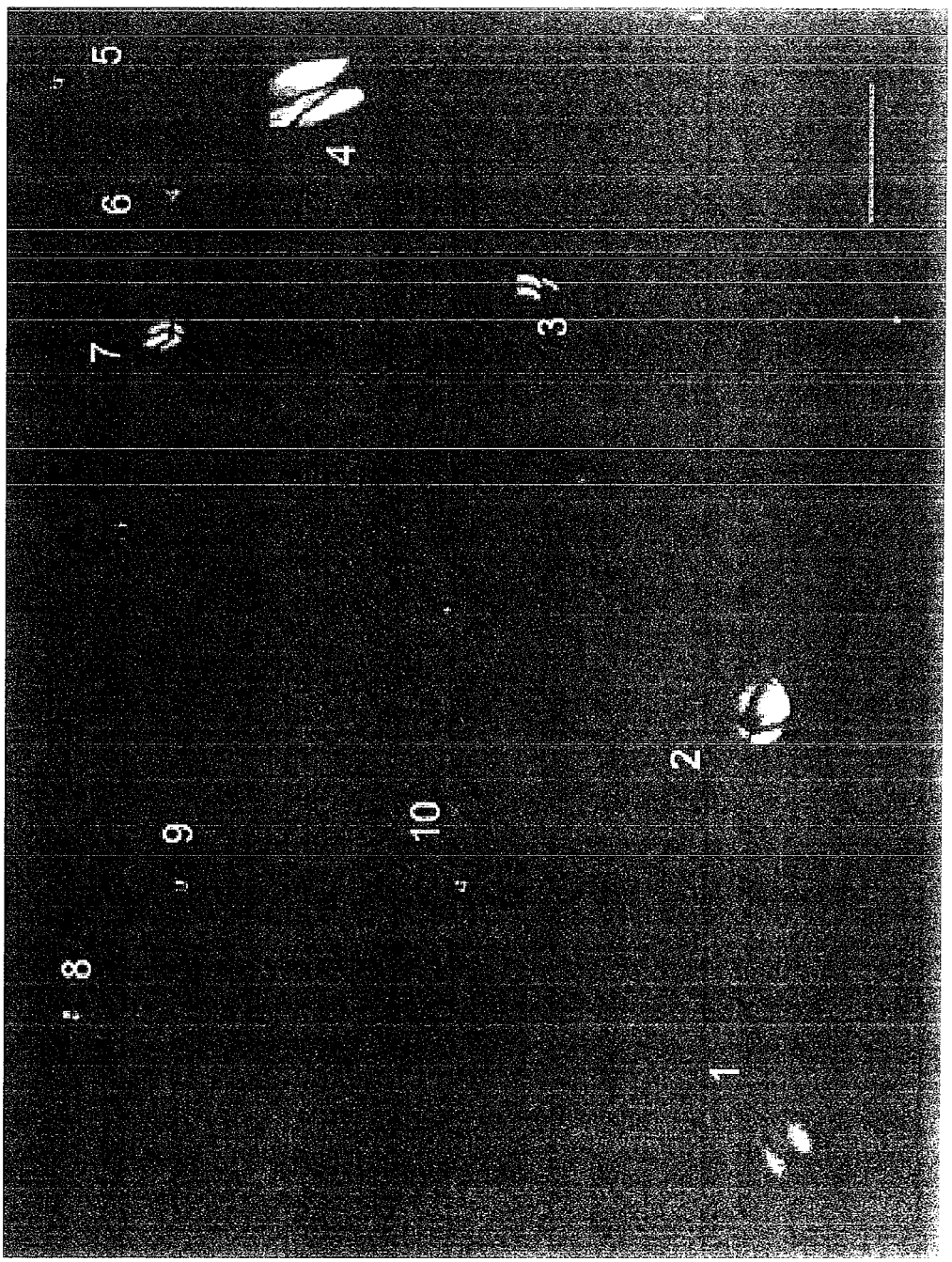
FIG. 9b is a drawing showing an optical microscope photograph of the particle morphology of processed starch J swollen in water (Comparative Example 7) (polarized)

The processed starch J had a part of the particles with broken outer shell structure without preserving the shape of the primary particle which is the same constituent unit as the natural starch grain and some of the primary particles were not individually distinguishable (see FIG. 9(a)). Further, in the swollen state in water, a large number of the non swelling starch particles showing a distinct polarized cross as in a natural starch existed (See FIG. 9(b)). Potato starch has a wide range of the particle size distribution in which large particles easily gelatinized and small particles hardly gelatinized by heat treatment are mixed together. For this reason, when potato starch was heat-treated at 68° C., which is higher than the gelatinization onset temperature of 61° C., the small particles were not gelatinized and particles in which a polarized cross is distinctly shown are remained. Further, the large particles swelled so much that the outer shell structure was broken. The tablets in any of the tablet compression methods in which the processed starch J was used only had slower disintegration time compared with the processed starches A to E.

Comparative Example 8

Figure 10A:
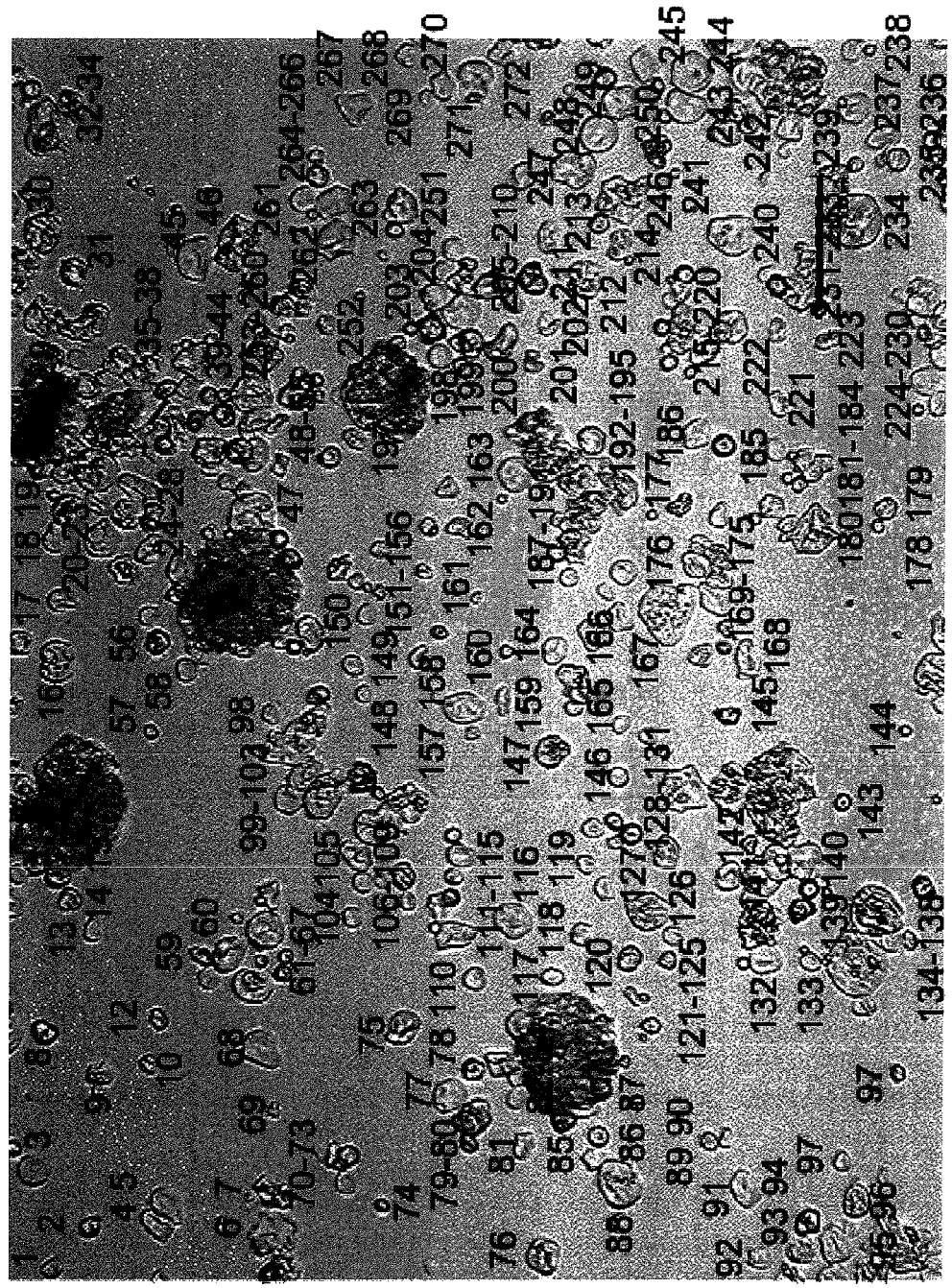
FIG. 10a is a drawing showing an optical microscope photograph of the particle morphology of partly pregelatinized starch PCS swollen in water (Comparative Example 8) (not polarized)
Figure 10B:
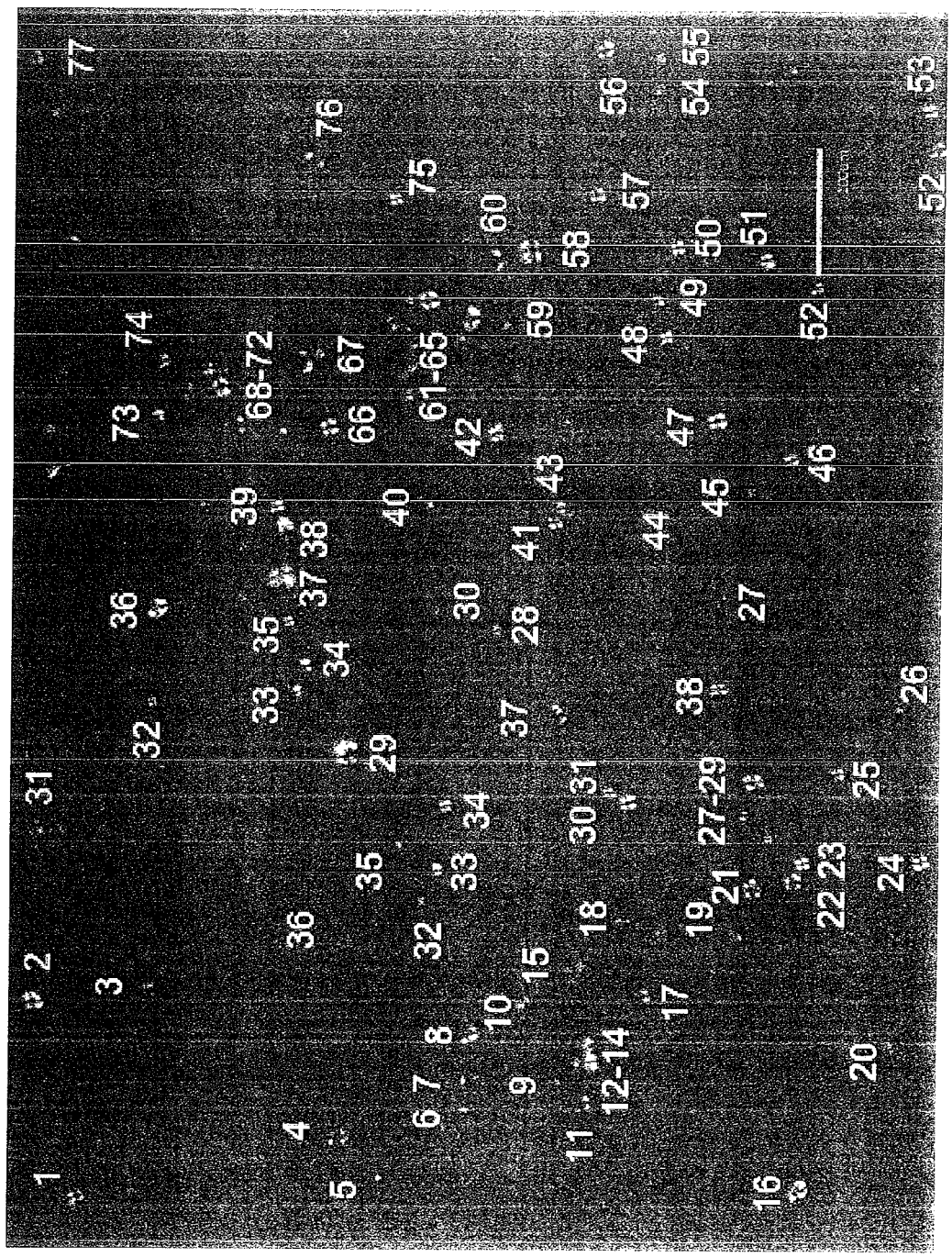
FIG. 10b is a drawing showing an optical microscope photograph of the particle morphology of partly pregelatinized starch PCS swollen in water (Comparative Example 8) (polarized)

Tablets were prepared by three methods, direct compression, high shear granulation/compression and fluidized bed granulation/compression, in the same manner as in Example 1 except that a commercially available partly pregelatinized starch (PCS, manufactured by SANWA CORNSTARCH CO., LTD.) was used and the disintegration test was carried out. The basic physical properties of the partly pregelatinized starch were shown in Table 1 and the optical microscope images of the particle shape in the swollen state in water were shown in FIGS. 10(a) and (b) ((b) is a polarized photograph). The result of the disintegration test was shown in Table 2.

The partly pregelatinized starch is obtained by mixing cornstarch and water to prepare a slurry, treated at a temperature 10° C. more than the gelatinization onset temperature (66.8° C./Denpun Kagaku Handbook ("Starch Chemistry Handbook" in Japanese), p. 36) or lower, allowing the starch grains to swell without braking the particle shape, following by drying. It is characterized that the outer shell structure of the starch particle remains unbroken. The proportion of the nonbirefringent particles in the swollen state in water was 72%. (See FIG. 10(a), (b)).

The partly pregelatinized starch had the swelling ratio of the primary particles in the dry state to the primary particles in the swollen state in water slightly beyond the range of the present invention (see Table 1). The obtained tablets in any of the tablet compression methods in which such a partly pregelatinized starch was used only had slower disintegration time compared with the processed starches A to E.

Comparative Example 9

Tablets were prepared by three methods, direct compression, high shear granulation/compression and fluidized bed granulation/compression, in the same manner as in Example 1 except that a commercially available partly pregelatinized starch (Starch 1500) was used in place of the processed starch A, and the disintegration test was carried out. The basic physical properties of the partly pregelatinized starch were shown in Table 1, and the optical microscope images of the particle shape in the swollen state in water were shown in FIGS. 11(a) and (b) ((b) is a polarized photograph). The result of the disintegration test was shown in Table 2.

The partly pregelatinized starch is obtained by a step of applying a pressure to a starch material in the presence of water at a gelatinization onset temperature or lower using a differential roller flour mill, parallel roller flour mill, extruder or the like, to break a part of the starch particles and compacting a mixture of the broken starch particles and the unbroken starch particles, followed by a step of crushing and sizing (corresponding to PATENT DOCUMENTS 13 and 14).

Figure 11A:
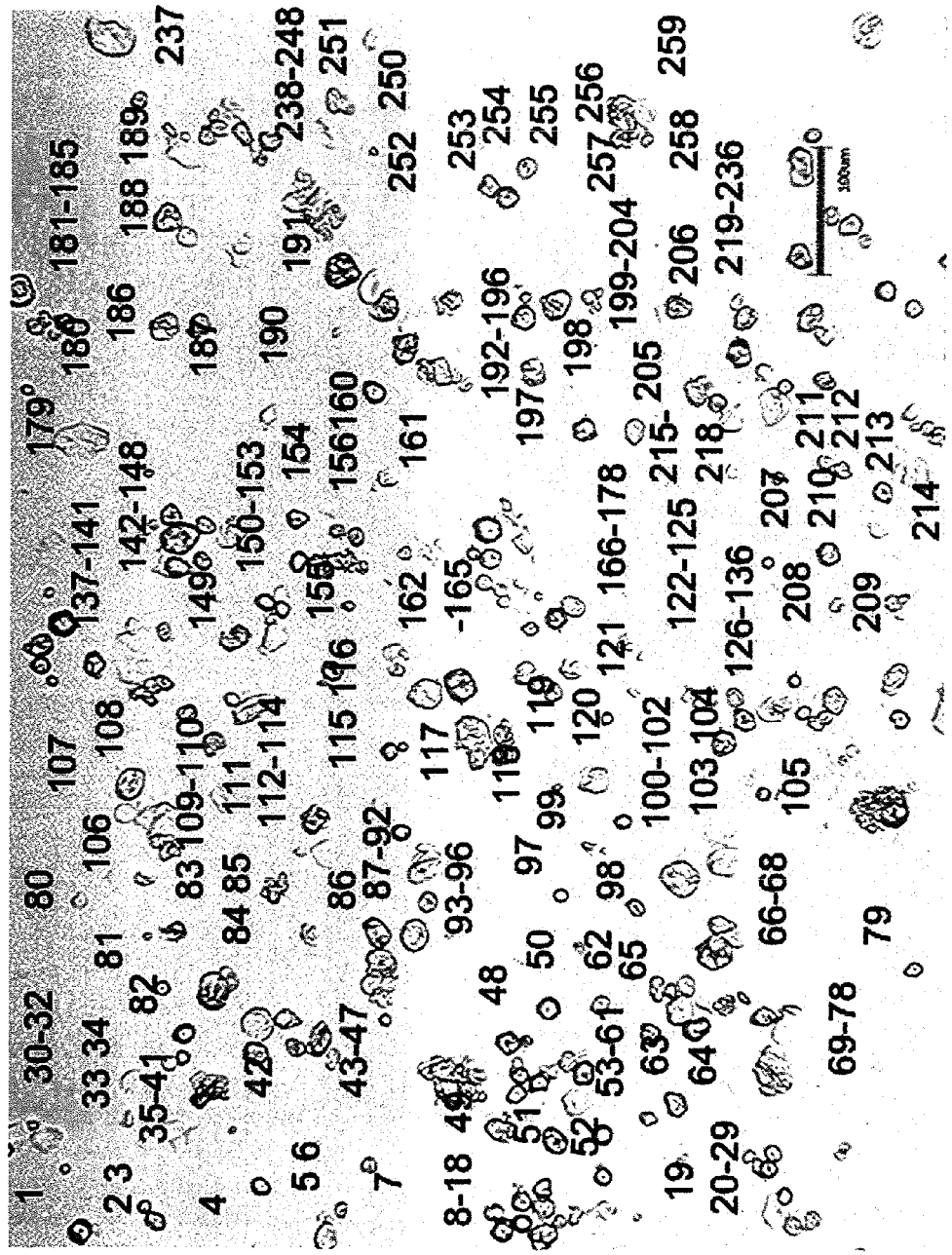
FIG. 11a is a drawing showing an optical microscope photograph of the particle morphology of partly pregelatinized starch Starch 1500 swollen in water (Comparative Example 9) (not polarized)
Figure 11B:
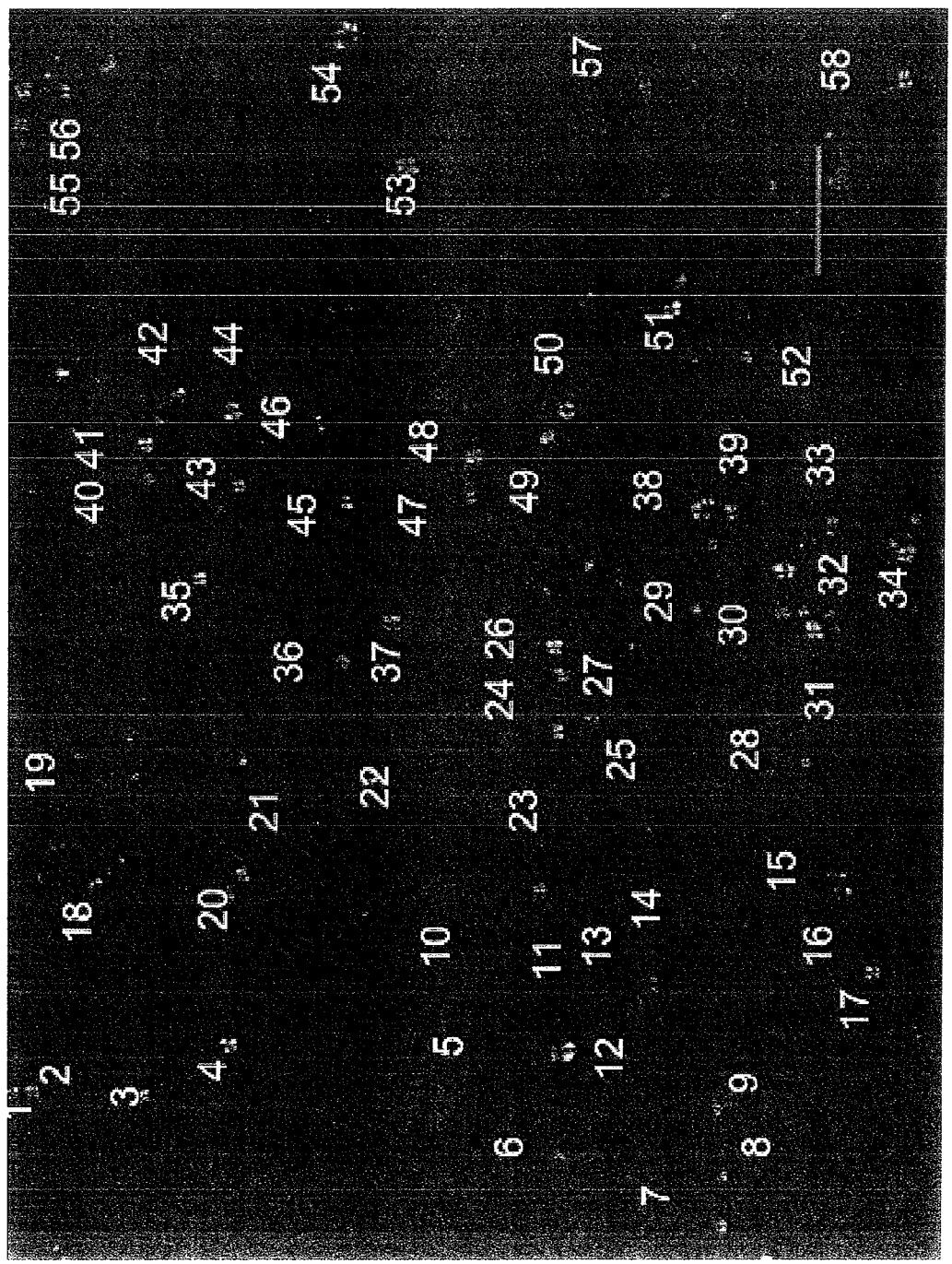
FIG. 11b is a drawing showing an optical microscope photograph of the particle morphology of partly pregelatinized starch Starch 1500 swollen in water (Comparative Example 9) (polarized)

The partly pregelatinized starch had the water soluble component amount greatly beyond the range of the present invention (see Table 1), and the proportion of the nonbirefringent particle in the swollen state in water was 78% (see FIGS. 11(a) and (b)).

The obtained tablets in any of the tablet compression methods in which such a partly pregelatinized starch was used only had slower disintegration time compared with the processed starches A to E.

Comparative Example 10

Tablets were prepared by three methods, direct compression, high shear granulation/compression and fluidized bed granulation/compression, in the same manner as in Example 1 except that croscarmellose sodium, a commercial super disintegrant (Kiccolate ND-2HS, manufactured by Asahi Chemical Co., Ltd.), was used, and the results of the disintegration test conducted were shown in Table 2. The tablets in which croscarmellose sodium was used as a disintegrant had fast disintegration time which was equivalent to that of the processed starches A to E.

Comparative Example 11

Tablets were prepared by three methods, direct compression, high shear granulation/compression and fluidized bed granulation/compression, in the same manner as in Example 1 except that crospovidone, a commercial disintegrant (Polyplasdone XL-10, manufactured by ISP Ltd.), was used and the results of the disintegration test conducted were shown in Table 2. The tablets in which crospovidone was used as a disintegrant had fast disintegration time which was equivalent to that of the processed starches A to E.

Comparative Example 12

Tablets were prepared by three methods, direct compression, high shear granulation/compression and fluidized granulation/compression, in the same manner as in Example 1 except that sodium starch glycolate, a commercial super disintegrant (Primojel, manufactured by DMV International, corresponding to an etherified starch), was used and the results of the disintegration test conducted were shown in Table 2. The tablets in which sodium starch glycolate was used as a disintegrant had comparatively fast disintegration time, which was slower than the disintegration time of croscarmellose sodium, crospovidone and the processed starches A to E.

Comparative Example 13

Tablets were prepared by three methods, direct compression, high shear granulation/compression and fluidized bed granulation/compression, in the same manner as in Example 1 except that a low substituted hydroxypropyl cellulose, a commercial disintegrant (L-HPC, manufactured by Shin-Etsu Chemical Co., Ltd.) was used, and the results of the disintegration test conducted were shown in Table 2. The obtained tablets in which the low substituted hydroxypropyl cellulose was used as a disintegrant had the slower disintegration time compared with that of croscarmellose sodium, crospovidone and the processed starches A to E.

Example 6

The processed starch A and aminophylline (Wako Pure Chemical Industries) were uniformly mixed so as to give a weight ratio of 50/50, the powder mixture was placed in a glass container equipped with a steel top and stored for 18 weeks under an atmosphere of 40° C. The color changes of the powder mixture after 2, 8 and 18 weeks had passed were measured using a colorimeter (SE200, manufactured by JASCO Corporation), and the results were shown in FIG. 1 together with the results of the measurement conducted in the same manner in Comparative Examples 14 to 17 to be described later.

The whiteness degree of the powder mixture of the processed starch A and aminophylline were only slightly decreased and the mixture was hardly colored. The decrease level of whiteness degree was equivalent to that of crospovidone, and was significantly minimized compared with sodium starch glycolate, croscarmellose sodium and the low substituted hydroxypropyl cellulose.

Comparative Example 14

The storage test of the powder mixture was carried out in the same manner as in Example 6 except that croscarmellose sodium, a commercial super disintegrant (Kiccolate ND-2HS, manufactured by Asahi Kasei Chemicals Corporation) was used, and the results were shown in FIG. 1.

The powder mixture of croscarmellose sodium and aminophylline had a considerable decrease in the whiteness degree.

Comparative Example 15

The storage test of the powder mixture was carried out in the same manner as in Example 6 except that crospovidone, a commercial super disintegrant (Polyplasdone XL-10, manufactured by ISP) was used, and the results were shown in FIG. 1.

The whiteness degree of the powder mixture of crospovidone and aminophylline was only slightly decreased which was equivalent to the level of the processed starch A.

Comparative Example 16

The storage test of the powder mixture was carried out in the same manner as in Example 6 except that sodium starch glycolate, a commercial super disintegrant (Primojel, manufactured by DMV International), was used, and the results were shown in FIG. 1.

The powder mixture of sodium starch glycolate and aminophylline had a considerable decrease in the whiteness degree.

Comparative Example 17

The storage test of the powder mixture was carried out in the same manner as in Example 6 except that a low substituted hydroxypropyl cellulose, a commercial disintegrant (L-HPC, manufactured by Shin-Etsu Chemical Co., Ltd.), was used, and the results were shown in FIG. 1.

The powder mixture of the low substituted hydroxypropyl cellulose and aminophylline had a considerable decrease in the whiteness degree.

Example 7

The processed starch A and ascorbic acid (manufactured by BASF Japan) were uniformly mixed so as to give a weight ratio of 50/50, the powder mixture was placed in a glass container equipped with a steel top and stored for 18 weeks under an atmosphere of 40° C. The color changes of the powder mixture after 2, 8 and 18 weeks had passed were measured using a colorimeter (SE200, manufactured by JASCO Corporation), and the results were shown in FIG. 2 together with the results of the measurement conducted in the same manner in Comparative Examples 18 to 21 to be described later.

The whiteness degree of the powder mixture of the processed starch A and ascorbic acid was only slightly decreased and the mixture was hardly colored. The decrease level of whiteness degree was slightly lower than that of crospovidone, and was significantly minimized compared with sodium starch glycolate, croscarmellose sodium and the low substituted hydroxypropyl cellulose.

Comparative Example 18

Figure 2:
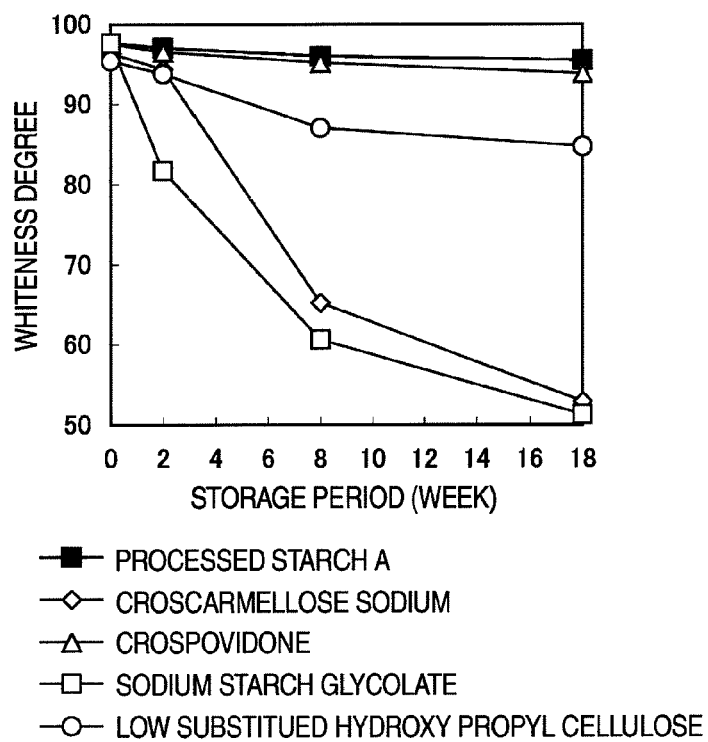
FIG. 2 is a drawing showing the time-dependent changes in the whiteness degree of an ascorbic acid tablet (Example 7, Comparative Examples 16 to 19)

The storage test of the powder mixture was carried out in the same manner as in Example 7 except that croscarmellose sodium, a commercial super disintegrant (Kiccolate ND-2HS, manufactured by Asahi Kasei Chemicals Corporation) was used, and the results were shown in FIG. 2.

The powder mixture of croscarmellose sodium and ascorbic acid developed intense coloring and had a considerable decrease in the whiteness degree.

Comparative Example 19

The storage test of the powder mixture was carried out in the same manner as in Example 7 except that crospovidone, a commercial super disintegrant (Polyplasdone XL-10, manufactured by ISP) was used, and the results were shown in FIG. 2.

The whiteness degree of the powder mixture of crospovidone and ascorbic acid was only slightly decreased, and the decrease level was slightly larger than the level of the processed starch A.

Comparative Example 20

The storage test of the powder mixture was carried out in the same manner as in Example 7 except that sodium starch glycolate, a commercial super disintegrant (Primojel, manufactured by DMV International) was used, and the results were shown in FIG. 2.

The powder mixture of sodium starch glycolate and ascorbic acid developed a considerable coloring and the whiteness degree was significantly decreased.

Comparative Example 21

The storage test of the powder mixture was carried out in the same manner as in Example 7 except that a low substituted hydroxypropyl cellulose, a commercial disintegrant (L-HPC, manufactured by Shin-Etsu Chemical Co., Ltd.), was used, and the results were shown in FIG. 2.

The powder mixture of the low substituted hydroxypropyl cellulose and ascorbic acid developed a considerable coloring and the whiteness degree was significantly decreased.

Example 8

The processed starch A and aspirin (Wako Pure Chemical Industries) were uniformly mixed so as to give a weight ratio of 80/20, the mixture was compacted using a static pressure press (MODEL-1321DW CREEP (trade name)/manufactured by Aiko Engineering Co., Ltd.) at a compressive force of 50 MPa to obtain a tablet having a diameter of 0.8 cm and a weight of 0.225 g. Three of the obtained tablets were put in a 100 ml test tube leaving the top open and stored for 2 weeks under an atmosphere having a temperature of 40° C. and a relative humidity of 70%. The thickness and hardness of the tablets were measured after 1 week and 2 weeks had passed, and the results were shown in FIGS. 3 and 4 together with the results of the measurement conducted in the same manner as in Comparative Examples 22 and 23 to be described later.

The aspirin tablet in which the processed starch A was used had little change in the tablet thickness even under an atmosphere having a temperature of 40° C. and a relative humidity of 70%, and the hardness was also controlled with a slight decrease.

Comparative Example 22

Figure 3:
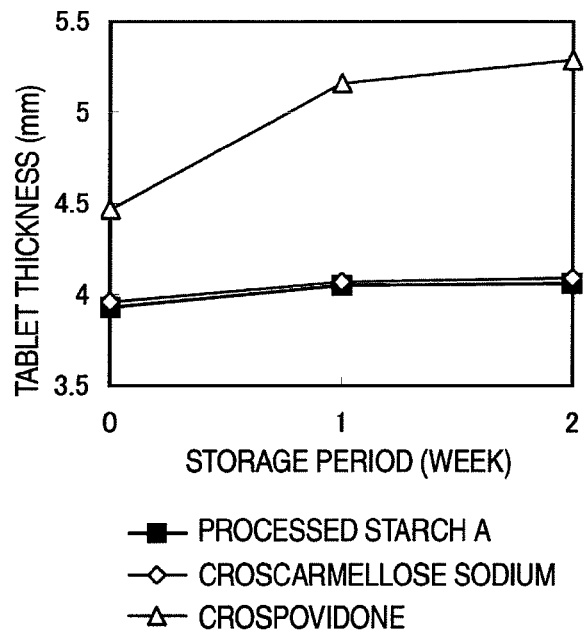
FIG. 3 is a drawing showing the time-dependent changes in the tablet thickness of an aspirin tablet (Example 8, Comparative Examples 20 and 21)
Figure 4:
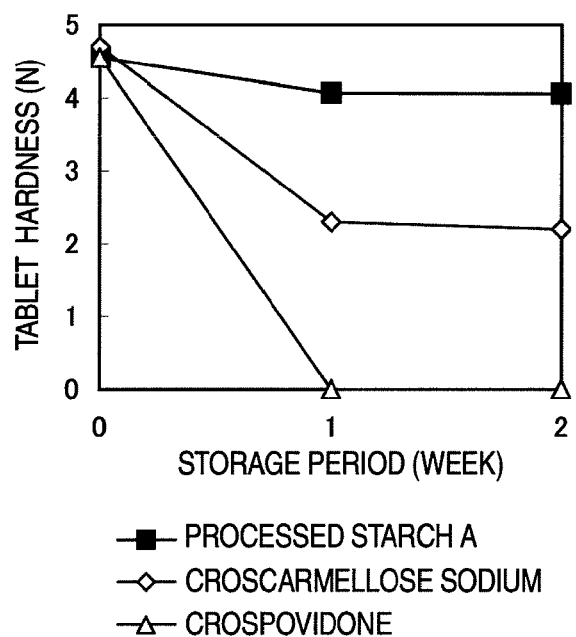
FIG. 4 is a drawing showing the time-dependent changes in the tablet hardness of an aspirin tablet (Example 8, Comparative Examples 20 and 21)

Tablet was prepared in the same manner as in Example 8 except that croscarmellose sodium, a commercial super disintegrant (Kiccolate ND-2HS (trade name), manufactured by Asahi Kasei Chemicals Corporation) was used, the storage test of the tablet was carried out and the results were shown in FIGS. 3 and 4.

The aspirin tablet in which croscarmellose sodium was used had a slight change in the tablet thickness, but had a significant decrease in hardness compared with the processed starch A.

Comparative Example 23

Tablet was prepared in the same manner as in Example 8 except that crospovidone, a commercial super disintegrant (XL-10, manufactured by ISP), was used and the storage test thereof was carried out, and the results were shown in FIGS. 3 and 4.

The aspirin tablet in which crospovidone was used swelled largely and became friable to the extent that the hardness could not be measured.

Example 9

The processed starch A, mannitol (mannite, manufactured by TOWA CHEMICAL INDUSTRY) and a microcrystalline cellulose ("CEOLUS" (registered trademark) KG-802) were uniformly mixed so as to give a weight ratio of 5/85/10, and the mixture was wet-granulated using pure water as a binder in a fluidized bed granulator (MP-01, manufactured by Powrex Corp.) under the condition of drying the mixture until an exhaust-air temperature reaches 40° C. in the spray conditions of, at the fluidized bed top spray and bottom spray, 0.1 MPa, 30 L/min, air flow rate 20 to 40 $m^3$/hr, charge-air temperature 75° C., exhaust-air temperature in due course (28 to 33° C.) and spray solution rate: about 12.5 g/min. The obtained granules were put in a sieve having an opening of 700 μm to remove the coarse particles whereby granules for the compression were obtained. Subsequently, the obtained granules for the compression was slowly mixed with magnesium stearate (manufactured by Taihei Chemical Industry Co., Ltd.) so as to give a weight ratio of 100/0.5 (the granules/magnesium stearate) to formulate an orally disintegratable tablet having a diameter of 8.0 mm and a weight of 0.18 g using a rotary tablet press (Clean Press Collect 12HUK (trade name)/manufactured by Kikusui Seisakusho Co., Ltd.) at pressures of 50, 80, 100 and 120 MPa. Using the tablets having a hardness of almost 50 N out of the obtained tablets, sensory evaluation was performed by 10 people to study the disintegration time in the mouth, texture and swallowness were examined, and the results were shown in Table 3 together with the results of the similar studies for Comparative Examples 24 and 25 to be described later.

The processed starch A was free of disagreeable flavor with good texture. The processed starch A had the disintegration time rather slower than crospovidone, but was preferably received than croscarmellose sodium and crospovidone by reason of being free of disagreeable flavor in terms of the "swallowness".

Comparative Example 24

An orally disintegratable tablet was prepared in the same manner as in Example 9 except that croscarmellose sodium, a commercial super disintegrant (Kiccolate ND-2HS (trade name), manufactured by Asahi Kasei Chemicals Corporation) was used, the evaluation was carried out, and the results were shown in Table 3.

Croscarmellose sodium had a lingering sensation in the mouth and throat in addition to unsmoothness and stickiness, and was hence not preferable in texture. Additionally, the disintegration time was slower compared with the processed starch A and crospovidone.

Comparative Example 25

An orally disintegratable tablet was prepared in the same manner as in Example 9 except that crospovidone, a commercial super disintegrant (XL-10, manufactured by ISP) was used, the evaluation was carried out, and the results were shown in Table 3. Crospovidone had a good texture, but had rather unsmoothness and stickiness. Crospovidone had the fastest disintegration time compared with the processed starch A and croscarmellose sodium but had poorer swallowness than the processed starch A.

TABLE 1

| | Sample name | Water retention capacity (%) | Water soluble component amount (%) | Sedimentation volume (cm$^3$/g) | Average particle size of primary particles in dry state (μm) |
|---|---|---|---|---|---|
| Example 1 | Processed Starch A | 610 | 2.4 | 7.1 | 28 |
| Example 2 | Processed Starch B | 730 | 5.4 | 9.0 | 32 |
| Example 3 | Processed Starch C | 820 | 6.9 | 11.1 | 32 |
| Example 4 | Processed Starch D | 1110 | 7.4 | 13.2 | 41 |
| Example 5 | Processed Starch E | 1270 | 9.7 | 17.0 | 50 |
| Comparative Example 1 | Processed Starch F | 350 | 3.2 | 8.5 | 25 |
| Comparative Example 2 | Processed Starch G | 530 | 2.1 | 5.6 | 27 |
| Comparative Example 3 | Processed Starch H | 1350 | 11.1 | 22.0 | 55 |
| Comparative Example 4 | Processed Starch K | 1360 | 10.6 | 18.8 | 53 |
| Comparative Example 5 | Processed Starch I | 1420 | 58.1 | 30.0 | 57 |
| Comparative Example 6 | Processed Starch L | 580 | 2.3 | 7.5 | 19 |
| Comparative Example 7 | Processed Starch J | 620 | 9.9 | 13.0 | 45 |
| Comparative Example 8 | Partly pregelatinized starch (PCS) | 570 | 2.1 | 7.2 | 26 |
| Comparative Example 9 | Partly pregelatinized starch (Starch 1500) | 410 | 13.6 | 7.0 | 17 |

| | Average particle size of primary particles in swollen state in water (μm) | Swelling ratio | Presence of particle breakage | Percentage of nonbirefringent particles (%) |
|---|---|---|---|---|
| Example 1 | 48 | 1.7 | None | 94.5 |
| Example 2 | 65 | 2.0 | None | 95 |
| Example 3 | 76 | 2.4 | None | 96 |
| Example 4 | 82 | 2.0 | None | 97 |
| Example 5 | 110 | 2.2 | None | 98 |
| Comparative Example 1 | 36 | 1.4 | None | 78 |
| Comparative Example 2 | 37 | 1.4 | None | 81 |
| Comparative Example 3 | Not measureable due to particle breakage | Not measureable due to particle breakage | Breakage found | — |
| Comparative Example 4 | 154 | 2.9 | Minor breakage found | — |
| Comparative Example 5 | Not measureable due to particle breakage | Not measureable due to particle breakage | Breakage found | — |
| Comparative Example 6 | 28 | 1.5 | None | 82 |
| Comparative Example 7 | Not measureable due to particle breakage | Not measureable due to particle breakage | Breakage found | — |
| Comparative Example 8 | 34 | 1.3 | None | 72 |
| Comparative Example 9 | 20 | 1.2 | Not measurable due to particle engagement | 78 |

TABLE 2

| | | Direct Compression | | | | High shear granulation/Compression | |
|---|---|---|---|---|---|---|---|
| | | Compression force 5 kN | | Compression force 8 kN | | Compression force 8 kN | |
| | | Tablet hardness (N) | Disintegration time (s) | Tablet hardness (N) | Disintegration time (s) | Tablet hardness (N) | Disintegration time (s) |
| Example 1 | Processed Starch A | 46 | 20 | 89 | 54 | 60 | 36 |
| Example 2 | Processed Starch B | 53 | 16 | 91 | 37 | 63 | 30 |
| Example 3 | Processed Starch C | 51 | 21 | 91 | 44 | 61 | 29 |
| Example 4 | Processed Starch D | 50 | 20 | 88 | 58 | 60 | 35 |
| Example 5 | Processed Starch E | 54 | 21 | 94 | 64 | 65 | 39 |
| Comparative Example 1 | Processed Starch F | 48 | 37 | 78 | 390 | 60 | 71 |
| Comparative Example 2 | Processed Starch G | 50 | 32 | 89 | 210 | 62 | 48 |
| Comparative Example 3 | Processed Starch H | 52 | 34 | 90 | 132 | 66 | 54 |
| Comparative Example 4 | Processed Starch K | 55 | 35 | 91 | 144 | 64 | 50 |
| Comparative Example 5 | Processed Starch I | 56 | 76 | 96 | 600 or longer | 72 | 116 |
| Comparative Example 6 | Processed Starch L | 41 | 30 | 79 | 181 | 53 | 59 |
| Comparative Example 7 | Processed Starch J | 50 | 29 | 91 | 371 | 60 | 69 |
| Comparative Example 8 | Partly pregelatinized starch (PCS) | 48 | 31 | 88 | 340 | 55 | 66 |
| Comparative Example 9 | Partly pregelatinized starch (Starch 1500) | 58 | 54 | 95 | 342 | 62 | 64 |
| Comparative Example 10 | Croscarmellose sodium | 54 | 34 | 87 | 41 | 52 | 54 |
| Comparative Example 11 | Crospovidone | 59 | 16 | 92 | 31.8 | 65 | 31 |
| Comparative Example 12 | Sodium starch glycolate | 54 | 32 | 95 | 112 | 61 | 43 |
| Comparative Example 13 | Low substituted hydroxypropyl cellulose | 43 | 41 | 87 | 276 | 57 | 77 |

| | High shear granulation/Compression | | Fluidized bed granulation/Compression | | | |
|---|---|---|---|---|---|---|
| | Compression force 10 kN | | Compression force 5 kN | | Compression force 7 kN | |
| | Tablet hardness (N) | Disintegration time (s) | Tablet hardness (N) | Disintegration time (s) | Tablet hardness (N) | Disintegration time (s) |
| Example 1 | 80 | 60 | 57 | 76 | 94 | 122 |
| Example 2 | 83 | 52 | 59 | 66 | 97 | 110 |
| Example 3 | 85 | 49 | 63 | 60 | 100 | 103 |
| Example 4 | 82 | 55 | 63 | 71 | 96 | 119 |
| Example 5 | 91 | 58 | 60 | 87 | 101 | 128 |
| Comparative Example 1 | 79 | 245 | 55 | 100 | 92 | 205 |
| Comparative Example 2 | 76 | 112 | 58 | 106 | 93 | 201 |
| Comparative Example 3 | 88 | 196 | 62 | 99 | 99 | 192 |
| Comparative Example 4 | 90 | 216 | 61 | 97 | 97 | 200 |
| Comparative Example 5 | 98 | 411 | 65 | 136 | 104 | 387 |
| Comparative Example 6 | 69 | 151 | 51 | 92 | 86 | 176 |
| Comparative Example 7 | 78 | 223 | 61 | 116 | 89 | 236 |
| Comparative Example 8 | 77 | 196 | 59 | 104 | 91 | 212 |
| Comparative Example 9 | 82 | 216 | 63 | 107 | 97 | 253 |
| Comparative Example 10 | 70 | 61 | 61 | 98 | 96 | 118 |
| Comparative Example 11 | 81 | 36 | 60 | 143 | 101 | 112 |
| Comparative Example 12 | 86 | 103 | 63 | 82 | 98 | 168 |
| Comparative Example 13 | 78 | 196 | 54 | 149 | 139 | 231 |

TABLE 3

| | | Disintegration time (sec) | Texture | Order of "Swallowness" |
|---|---|---|---|---|
| Example 9 | Processed starch A | 16 | Free of disagreeable flavor, good texture | 1 |
| Comparative Example 24 | Croscarmellose sodium | 18 | Unsmoothness and stickiness, lingering sensation in mouth/throat, not preferable | 3 |
| Comparative Example 25 | Crospovidone | 10 | Good texture but rather unsmooth/sticky | 2 |

INDUSTRIAL APPLICABILITY

Since the processed starch powder of the present invention has a low reactivity to an active ingredient and hygroscopicity, it is used in the uses of pharmaceuticals, agricultural chemical, fertilizers, feed, food, industries, cosmetics, etc., as a disintegrant of a natural material origin which has good preparation storage stability as well as having been commonly eaten and is highly safe.

The invention claimed is:

1. A processed starch powder having a water soluble component amount of more than 2% by weight and less than 10% by weight and a water retention capacity of more than 600% and 1500% or less, and being a nonbirefringent particle, wherein 90% or more of the starch particles, in terms of the particle number, maintain the shape derived from a natural starch when observed using an optical microscope.

2. The processed starch powder according to claim 1, wherein an average particle size of primary particles is 25 to 80 μm in a dry state and an average particle size of primary particles is 45 to 160 μm in a swollen state in water.

3. The processed starch powder according to claim 1, which is obtained without chemically treating a natural starch material having an amylose content of 20% by weight or more and less than 30% by weight.

4. The processed starch powder according to claim 1, wherein the average particle size of primary particles of dry particles is larger than that of a natural starch material.

5. The processed starch powder according to claim 1, wherein the natural starch material is potato starch.

6. The processed starch powder according to claim 1, which is obtained by a process comprising the steps of (i) heat-treating a natural starch material using steam at 100 to 130° C. under reduced pressure conditions, (ii) preparing the heat-treated starch material into a starch slurry having a solid content of 1 to 20% by weight, (iii) heat-treating the starch slurry in a temperature range from more than a temperature of 10° C. higher than a gelatinization onset temperature intrinsic to starch to less than 90° C., and (iv) subsequently, drying the heat-treated starch slurry.

7. The processed starch powder according to claim 1, wherein a sedimentation volume is 7 $cm^3$/g or more and 20 $cm^3$/g or less.

8. The processed starch powder according to claim 1, wherein a swelling ratio of the primary particles in the dry state to the primary particles in the swollen state in water is 1.5 to 5.0.

9. The processed starch powder according to claim 1, wherein the processed starch powder is a disintegrant.

10. A composition comprising the processed starch powder according to claim 1 and one or more active ingredients.

11. The composition according to claim 10 having a hardness of 100±10 N and a disintegration time of 70 seconds or less when obtained by direct compression.

12. The composition according to claim 10 having a hardness of 100±10 N and a disintegration time of 60 seconds or less when obtained by compression after high shear granulation.

13. The composition according to claim 10 having a hardness of 100±10 N and a disintegration time of 130 seconds or less when obtained by compression after fluidized bed granulation.

14. The composition according to claim 10 comprising 0.2 to 5% by weight of the processed starch powder in the composition.

15. The composition according to claim 10, wherein the one or more active ingredients are selected from active pharmaceutical ingredients or food ingredients.

16. A process for manufacturing the processed starch powder according to claim 1, the process comprising the steps of (i) heat-treating a natural starch material using steam at 100 to 130° C. under reduced pressure conditions, (ii) preparing the heat-treated starch material into a starch slurry having a solid content of 1 to 20% by weight, (iii) heat-treating the starch slurry in a temperature range from more than a temperature of 10° C. higher than a gelatinization onset temperature intrinsic to starch to less than 90° C., and (iv) subsequently, drying the heat-treated starch slurry.

\* \* \* \* \*